(12) United States Patent
Jeong et al.

(10) Patent No.: US 11,684,762 B2
(45) Date of Patent: Jun. 27, 2023

(54) ENERGY SELF-SUFFICIENT REAL TIME BIO-SIGNAL MONITORING AND NUTRIENT DELIVERY SYSTEM BASED ON SALINITY GRADIENT POWER GENERATION

(71) Applicant: KOREA INSTITUTE OF ENERGY RESEARCH, Daejeon (KR)

(72) Inventors: Nam-Jo Jeong, Jeju-si (KR); Ji Yeon Choi, Jeju-si (KR); Han-Ki Kim, Jeju-si (KR); Seung Cheol Yang, Jeju-si (KR); Kyo Sik Hwang, Jeju-si (KR); Ji-Hyung Han, Jeju-si (KR); Joo-Youn Nam, Jeju-si (KR); Eun-Jin Jwa, Jeju-si (KR); Soon-Chul Park, Jeju-si (KR); Yong-Seog Seo, Daejeon-si (KR); Moon-Seok Jang, Daejeon-si (KR)

(73) Assignee: KOREA INSTITUTE OF ENERGY RESEARCH, Daejeon (KR)

( * ) Notice: Subject to any disclaimer, the term of this patent is extended or adjusted under 35 U.S.C. 154(b) by 209 days.

(21) Appl. No.: 16/651,605

(22) PCT Filed: Feb. 2, 2018

(86) PCT No.: PCT/KR2018/001468
§ 371 (c)(1),
(2) Date: Mar. 27, 2020

(87) PCT Pub. No.: WO2019/132107
PCT Pub. Date: Jul. 4, 2019

(65) Prior Publication Data
US 2020/0316354 A1    Oct. 8, 2020

(30) Foreign Application Priority Data

Dec. 29, 2017  (KR) ........................ 10-2017-0184854
Feb. 1, 2018   (KR) ........................ 10-2018-0012895

(51) Int. Cl.
*A61M 37/00*    (2006.01)
*A61L 31/14*    (2006.01)
(Continued)

(52) U.S. Cl.
CPC .......... *A61M 37/00* (2013.01); *A61L 31/026* (2013.01); *A61L 31/146* (2013.01); *H01M 8/227* (2013.01);
(Continued)

(58) Field of Classification Search
CPC .. H01M 8/227; H01M 2250/30; A61M 37/00; A61M 2037/0007; A61M 2230/65;
(Continued)

(56) References Cited

U.S. PATENT DOCUMENTS 5,298,017 A * 3/1994 Theeuwes ............... A61N 1/30
604/20
5,637,084 A * 6/1997 Kontturi .............. A61N 1/0448
604/20
2012/0041288 A1* 2/2012 Essalik ............ A61B 5/150099
600/310

FOREIGN PATENT DOCUMENTS

KR    2018-0058438    6/2008
KR    2014-0058118    5/2014
(Continued)

OTHER PUBLICATIONS

Stoica, Daniela, et al. "Influence of fabrication procedure on the electrochemical performance of Ag/AgCl reference electrodes." Electrochimica acta 56.27 (2011): 10009-10015. (Year: 2011).*
(Continued)

*Primary Examiner* — Nilay J Shah
(74) *Attorney, Agent, or Firm* — Lex IP Meister, PLLC

(57) ABSTRACT

Disclosed is an energy self-sufficient real time bio-signal monitoring and nutrient and/or drug delivery system based
(Continued)

on salinity gradient power generation. The energy self-sufficient real time bio-signal monitoring and/or nutrient delivery system based on salinity gradient power generation includes: an electricity generation and nutrient and/or drug delivery module including a reverse electrodialysis device which generates electricity by using a nutrient and/or drug solution and discharge a diluted nutrient solution; and a bio-signal measuring unit inserted into the electricity generation and nutrient and/or drug delivery module and configured to receive electricity from the electricity generation and nutrient and/or drug delivery module and measure a bio-signal.

8 Claims, 31 Drawing Sheets

(51) Int. Cl.
*A61L 31/02* (2006.01)
*H01M 8/22* (2006.01)
*A61B 5/0531* (2021.01)
*A61N 1/30* (2006.01)

(52) U.S. Cl.
CPC .... *A61B 5/0531* (2013.01); *A61M 2037/0007* (2013.01); *A61M 2230/65* (2013.01); *A61N 1/30* (2013.01); *H01M 2250/30* (2013.01)

(58) Field of Classification Search
CPC ... A61L 31/026; A61L 31/146; A61B 5/0531; A61N 1/30
See application file for complete search history.

(56) References Cited

FOREIGN PATENT DOCUMENTS

KR  2017-0081838     7/2017
WO  WO-2016056778 A1 *  4/2016 ............ A61M 37/00

OTHER PUBLICATIONS

Patent translation of WO 2016056778 A1 (Year: 2016).*
Ki-Taek Kim et al., "Novel reverse electrodialysis-driven iontophoretic system for topical and transdermal delivery of poorly permeable therapeutic agents", Drug Delivery, Aug. 28, 2017, vol. 24, 1, pp. 1204-1215.

* cited by examiner

ENERGY SELF-SUFFICIENT REAL TIME BIO-SIGNAL MONITORING AND NUTRIENT DELIVERY SYSTEM BASED ON SALINITY GRADIENT POWER GENERATION

TECHNICAL FIELD

The present invention relates to an energy self-sufficient real time bio-signal monitoring and/or nutrient delivery system based on salinity gradient power generation.

BACKGROUND ART

In the case of iontophoresis technology for delivering nutrients and drugs to specific body tissues, power supply and nutrient supply are separated, so that there is a limitation in miniaturizing a device. As disclosed in Korean Patent No. 1772140, iontophoresis technology in a salinity gradient power generation power supply scheme that generates electricity by using a general salt solution (for example, $MgCl_2$, $AgCl$, $CuCl_2$, $CaCl_2$) containing NaCl has been developed, but the technology also adopts the scheme of supplying nutrients by using a separate component and does not have a separate real time bio-signal monitoring function.

Most of the real time bio-signal monitoring systems developed so far use alkaline batteries, lithium-ion batteries, lead storage batteries, and the like as portable power sources. However, those batteries are difficult to be manufactured in a flexible form that is recently required, and are not suitable for wearable monitoring systems, such as patches, due to safety problems.

DISCLOSURE

The present invention has been made in an effort to provide an energy self-sufficient nutrient delivery system based on salinity gradient power generation.

The present invention has also been made in an effort to provide an energy self-sufficient real time bio-signal monitoring system based on salinity gradient power generation.

The present invention has also been made in an effort to provide an energy self-sufficient real time bio-signal monitoring and nutrient delivery system based on salinity gradient power generation. An exemplary embodiment of the present invention provides an energy self-sufficient real time bio-signal monitoring and/or nutrient delivery system based on salinity gradient power generation, including: a reverse electrodialysis electricity generating device configured to generate electricity by using a nutrient and/or drug solution and discharge a diluted nutrient and/or drug solution; and a skin contact unit interposed between skin and a lower portion of a discharge part of the diluted nutrient and/or drug solution to deliver the diluted nutrient and/or drug solution.

Another exemplary embodiment of the present invention provides an energy self-sufficient real time bio-signal monitoring and/or nutrient delivery system based on salinity gradient power generation, including: a power supply unit formed of a reverse electrodialysis device; and a bio-signal measuring unit configured to receive electricity from the power supply unit and measure a bio-signal.

Still another exemplary embodiment of the present invention provides an energy self-sufficient real time bio-signal monitoring and/or nutrient delivery system based on salinity gradient power generation, including: an electricity generation and nutrient and/or drug delivery module including a reverse electrodialysis device which generates electricity by using a nutrient and/or drug solution and discharge a diluted nutrient solution; and a bio-signal measuring unit inserted into the electricity generation and nutrient and/or drug delivery module and configured to receive electricity from the electricity generation and nutrient and/or drug delivery module and measure a bio-signal.

The energy self-sufficient real time bio-signal monitoring and/or nutrient delivery system based on salinity gradient power generation according to the exemplary embodiments of the present invention may achieve energy self-sufficiency by using salinity gradient power generation. The energy self-sufficient real time bio-signal monitoring and/or nutrient delivery system based on salinity gradient power generation according to the exemplary embodiments of the present invention may simultaneously enable bio-signal measurement and/or absorption of useful materials in the body. Further, the energy self-sufficient real time bio-signal monitoring and/or nutrient delivery system based on salinity gradient power generation according to the exemplary embodiments of the present invention may be easily manufactured in a flexible form, so that it is possible to implement a monitoring and nutrient delivery system in a wearable form.

MODE FOR INVENTION

Hereinafter, the present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

Constituent elements which are not separately mentioned in relation to a salinity gradient power generation device (a reverse electrodialysis power generation device) and a bio-signal sensor may be appropriately selected and used by those skilled in the art according to a use purpose and condition if they have been used in the art. In addition, the terms, "unit", "module", and the like described in the specification mean units for processing at least one function and operation and can be implemented by hardware components or software components and combinations thereof.

Figure 1:
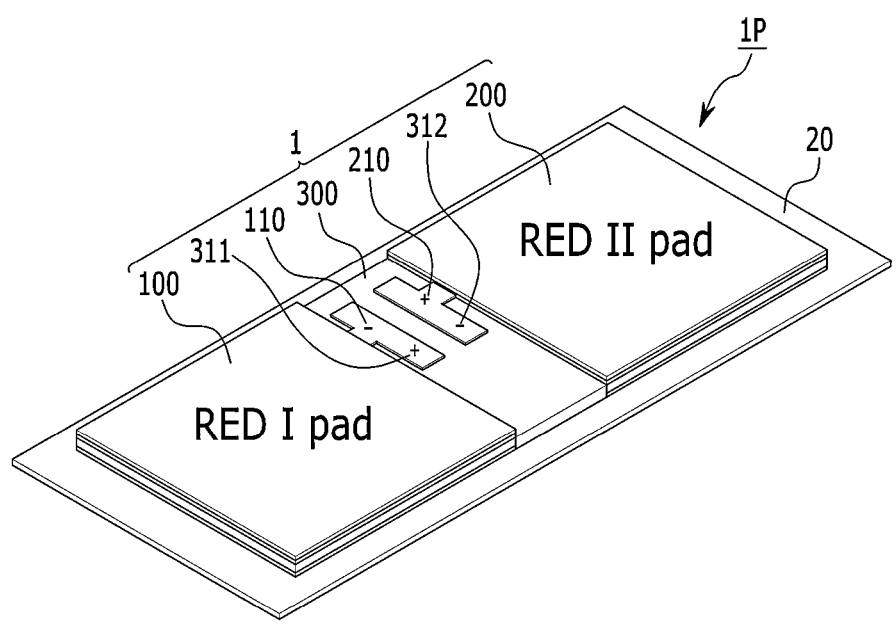
FIG. 1 is a perspective view of a patch before an energy self-sufficient real time bio-signal monitoring and nutrient delivery system based on salinity gradient power generation is attached to skin according to an exemplary embodiment of the present invention.
Figure 2:
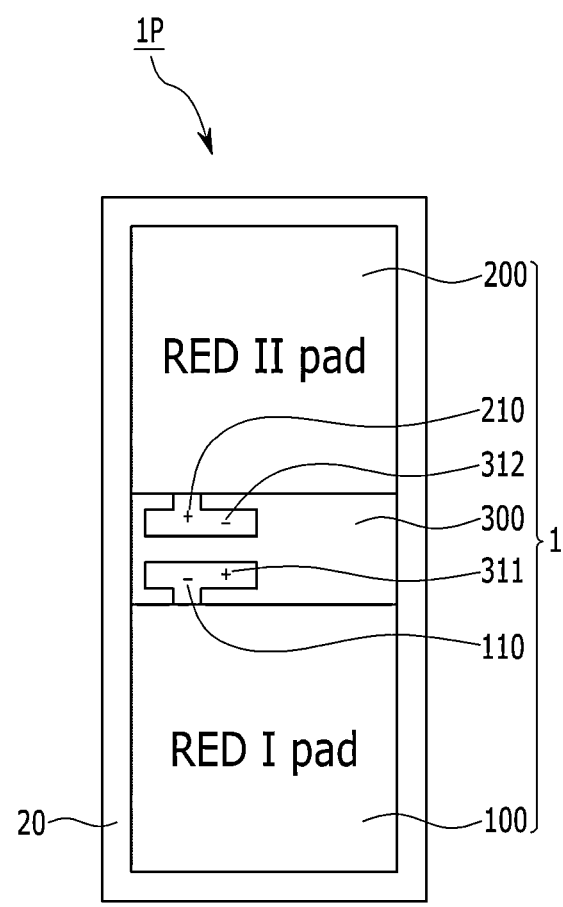
FIG. 2 is a top plan view of a patch before the energy self-sufficient real time bio-signal monitoring and nutrient delivery system based on salinity gradient power generation is attached to skin according to the exemplary embodiment of the present invention.
Figure 3:
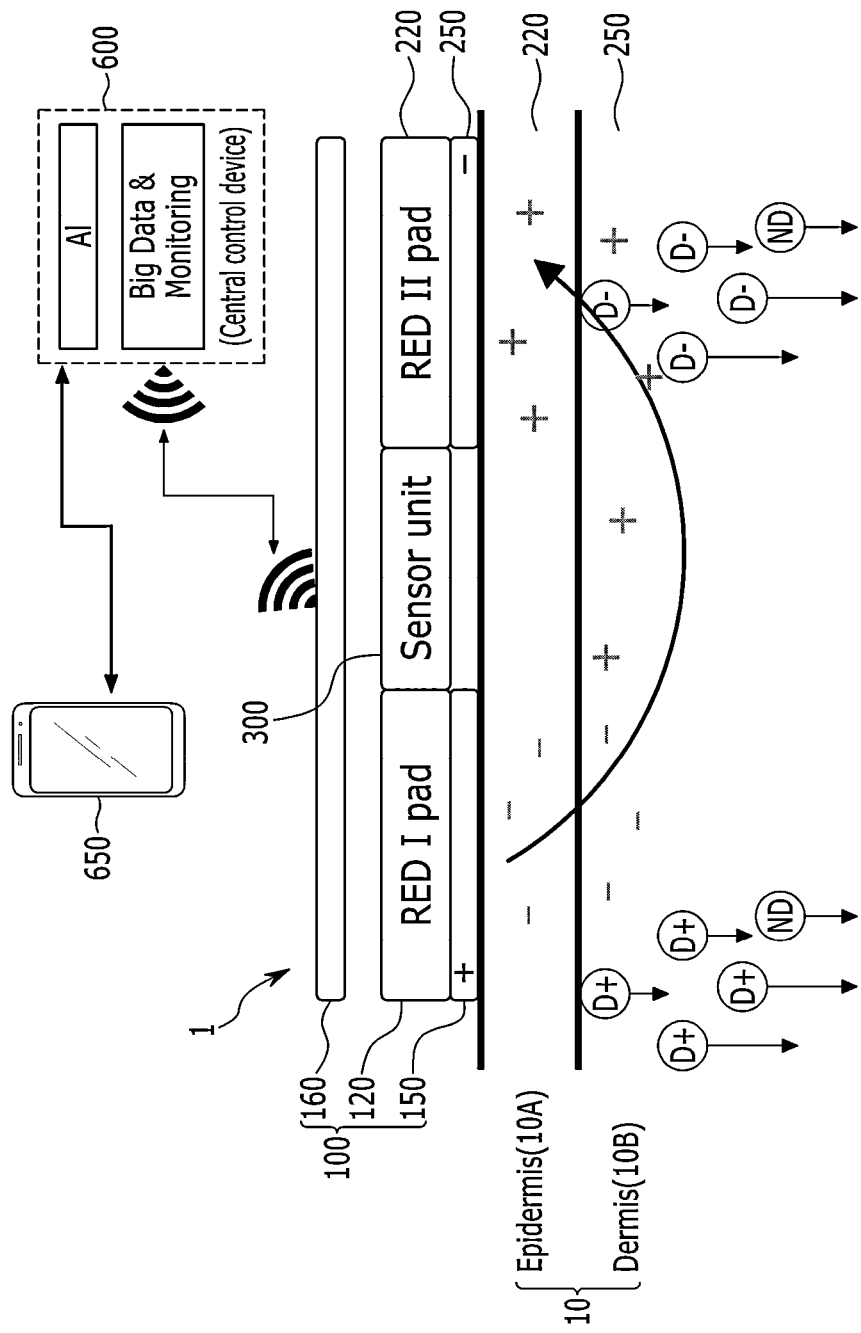
FIG. 3 is a cross-sectional view in the case where the energy self-sufficient real time bio-signal monitoring and nutrient delivery system based on salinity gradient power generation is attached to skin with a removal of an attachment pad according to the exemplary embodiment of the present invention.

FIGS. 1 and 2 are a perspective view and a top plan view of a patch 1P before an energy self-sufficient real time bio-signal monitoring and nutrient delivery system 1 is attached to skin, respectively, and FIG. 3 is a cross-sectional view in the case where the energy self-sufficient real time bio-signal monitoring and nutrient delivery system 1 is attached to skin 20 by using an attachment pad 20 according to an exemplary embodiment of the present invention.

Referring to FIGS. 1 through 3, the patch 1P is preserved or stored in the form in which the energy self-sufficient real time bio-signal monitoring and nutrient delivery system 1 is attached onto the attachment pad 20. Although not illustrated in the drawing, a pad (not illustrated) that is detachable just before the use may also be further included in the upper portion of the energy self-sufficient real time bio-signal monitoring and nutrient delivery system 1.

The system 1 includes a first electricity generation and nutrient and/or drug delivery module 100 and a second electricity generation and nutrient and/or drug delivery module 200 for supplying electricity for energy self-sufficiency and simultaneously supplying useful materials to the skin 10, a bio-signal measurement sensor unit 300 for monitoring a bio-signal in real time, and a central control device 600.

The first electricity generation and nutrient and/or drug delivery module 100 and the second electricity generation and nutrient and/or drug delivery module 200 are electrically connected with external input terminals 311 and 312 of the bio-signal measurement sensor unit 300 through external input terminals 110 and 210, respectively.

The central control device 600 may be electrically connected with the bio-signal measurement sensor unit 300 and the first electricity generation and nutrient and/or drug delivery module 100 and the second electricity generation and nutrient and/or drug delivery module 200, and may receive a detection signal of the bio-signal measurement sensor unit 300 and control the driving of the first electricity generation and nutrient and/or drug delivery module 100 and the second electricity generation and nutrient and/or drug delivery module 200 and the bio-signal measurement sensor unit 300 or communicate with a portable control device 650 of a user by a predetermined program as needed. The central control device 600 may analyze a state of a body according to the signal received from the sensor unit 300. Particularly, the central control device 600 may be an Artificial Intelligence (AI) based central control device which analyzes big data of a bio-signal based on AI and applies the analyzed data to the control again. Further, the central control device 600 may communicate the analyzed and monitored bio-signal with the portable control device 650 of the user.

The amounts of useful materials (D+, D−, ND) delivered through epidermis 10A and dermis 10B may be adjusted according to sizes of currents and voltages supplied through the first electricity generation and nutrient and/or drug delivery module 100 and the second electricity generation and nutrient and/or drug delivery module 200. D+ represents positively charged nutrients or drugs, D− represents negatively charged nutrients or drugs, and ND represents neutrally charged nutrients or drugs. Further, − and + represent counter ions of D+ and D−.

Figure 4:
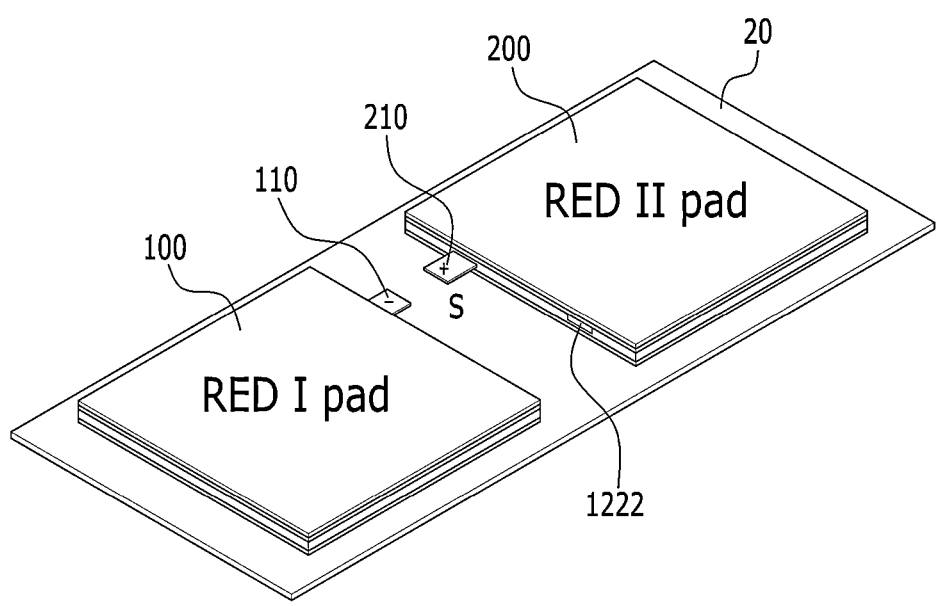
FIG. 4 is a perspective view of an electricity generation and nutrient and/or drug delivery module before a bio-signal measurement sensor unit is attached.
Figure 5:
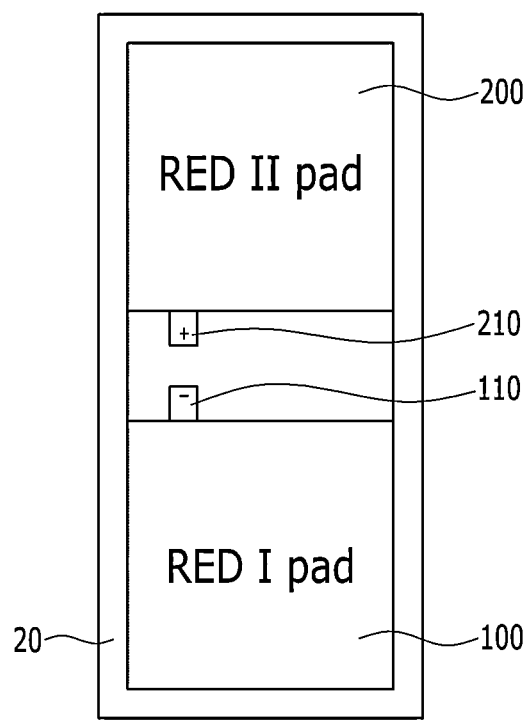
FIG. 5 is a top plan view of the electricity generation and nutrient and/or drug delivery module before the bio-signal measurement sensor unit is attached.
Figure 6:
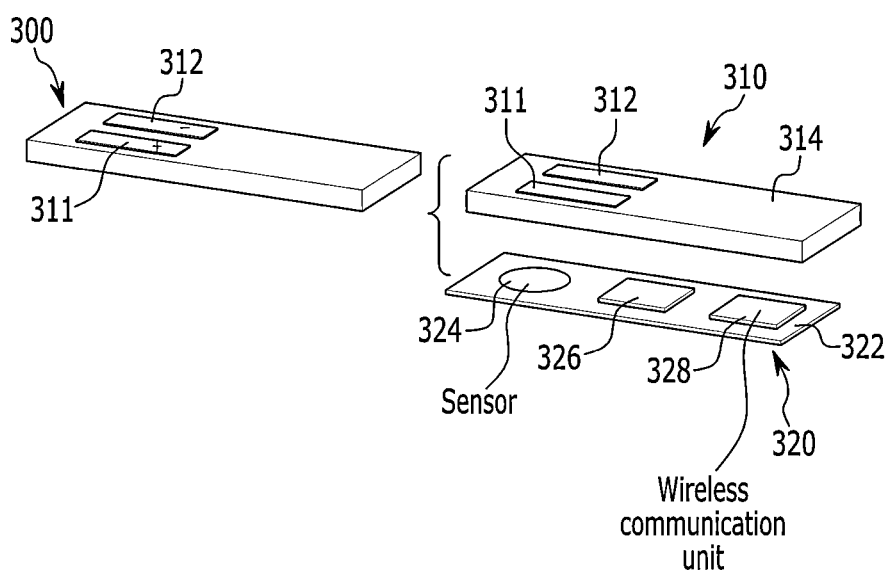
FIG. 6 is a schematic diagram illustrating the bio-signal measurement sensor unit detachable from the electricity generation and nutrient and/or drug delivery module.

FIGS. 4 and 5 are a perspective view and a top plan view of the electricity generation and nutrient and/or drug delivery module before the bio-signal measurement sensor unit 300 is attached, and FIG. 6 is a schematic diagram illustrating the bio-signal measurement sensor unit 300 conceived to be detachable from the electricity generation and nutrient and/or drug delivery module and be continuously usable.

Referring to FIGS. 4 and 5, the electricity generation and nutrient and/or drug delivery module includes a space (S), in which the bio-signal measurement sensor unit 300 is detachable between the external terminals 110 and 210 and the first electricity generation and nutrient and/or drug delivery module 100 and the second electricity generation and nutrient and/or drug delivery module 200. The bio-signal measurement sensor unit 300 may be detachable in the type in which the bio-signal measurement sensor unit 300 illustrated in FIG. 6 is inserted to the space S in which the bio-signal measurement sensor unit 300 is detachable. However, the foregoing form is merely the exemplary embodiment of the present invention, the insertion form of the sensor unit 300 may be modified and applied in various forms according to the structures of the first electricity generation and nutrient and/or drug delivery module 100 and the second electricity generation and nutrient and/or drug delivery module 200.

The bio-signal measurement sensor unit 300 may be permanently reusable unlike the electricity generation and nutrient and/or drug delivery module. The bio-signal measurement sensor unit 300 includes a current collector 310 and a sensor array 320 for receiving power from the electricity generation and nutrient and/or drug delivery module. The current collector 310 may be formed with external connection terminals 311 and 312, and the sensor array 320 may include a bio-signal measurement sensor 324, a signal processing unit 326 for amplifying and digital-converting the measurement signal of the sensor 324, and a wireless communication unit 328 for processing the digital-converted bio-signal according to a wireless communication standard and transmitting the processed bio-signal on a substrate 322. In this case, when the substrate 322 is formed of a flexible substrate (for example, a Flexible Printed Circuit Board (FPCB), the system may be implemented as a wearable system. Further, all of the components of the sensor may be patterned and manufactured in a form of a thin film.

As long as a sensor, such as a hear rate sensor, a body temperature sensor, a muscle microbehavior sensor, and a skin moisture content sensor, an electrolyte concentration sensor, and a blood sugar sensor using the discharged sweat, is suitable for the detection of a bio-signal that requires measurement by a contact with the skin, the sensor is usable as the sensor 324.

The signal processing unit 326 may include a current-voltage converting unit, an amplifying unit, a filter unit, an analog-digital converting unit, and the like.

The wireless communication unit 328 may be implemented with a short-range wireless communication standard, such as Bluetooth, ZigBee, Ultra WideBand (UWB), or Wi-Fi based on Institute of Electrical and Electronics Engineers (IEEE) 802.11, and process data provided from the signal processing unit 326 according to the wireless communication standard and transmit the processed bio-signal to the central control device 600 (see FIG. 3).

Figure 7:
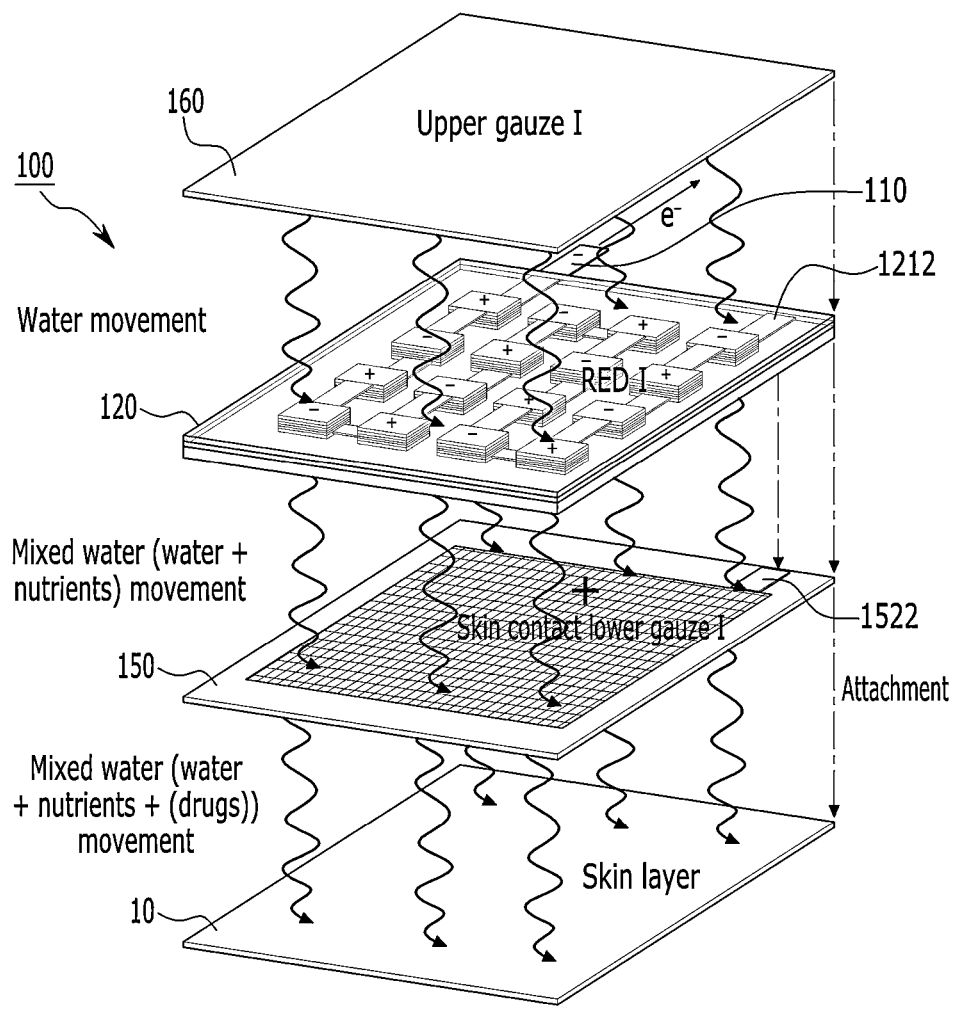
FIG. 7 is an exploded perspective view of a part of a first electricity generation and nutrient and/or drug delivery module before the bio-signal measurement sensor unit according to the exemplary embodiment of the present invention.
Figure 8:
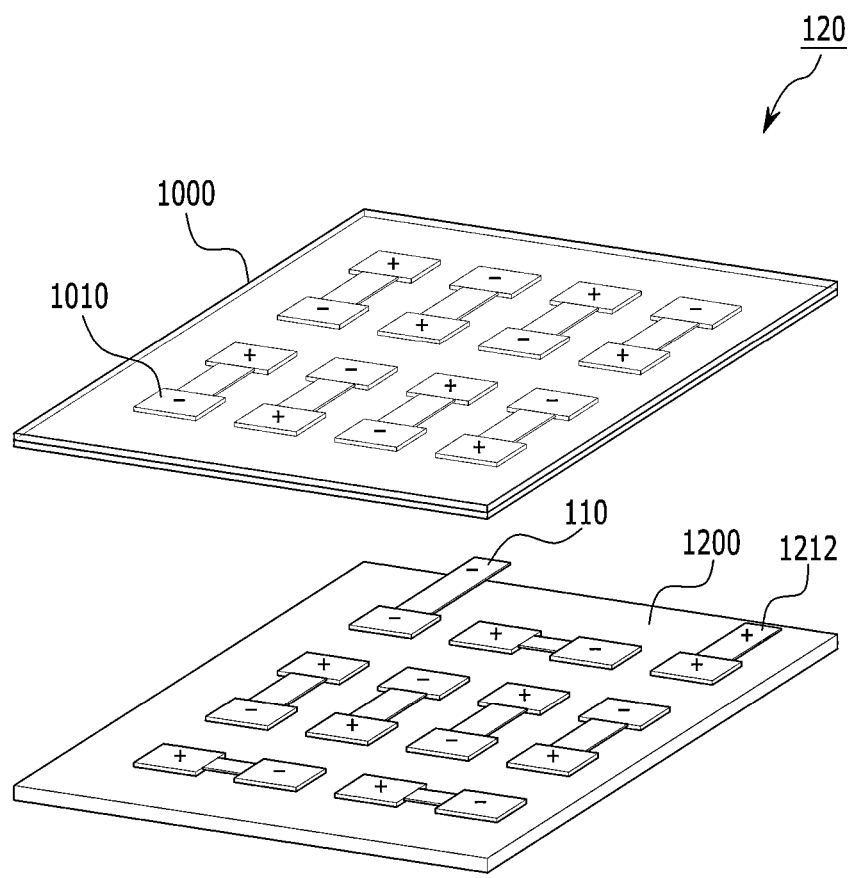
FIG. 8 is a perspective view of an electrode layer of a first reverse electrodialysis device according to the exemplary embodiment of the present invention.
Figure 9:
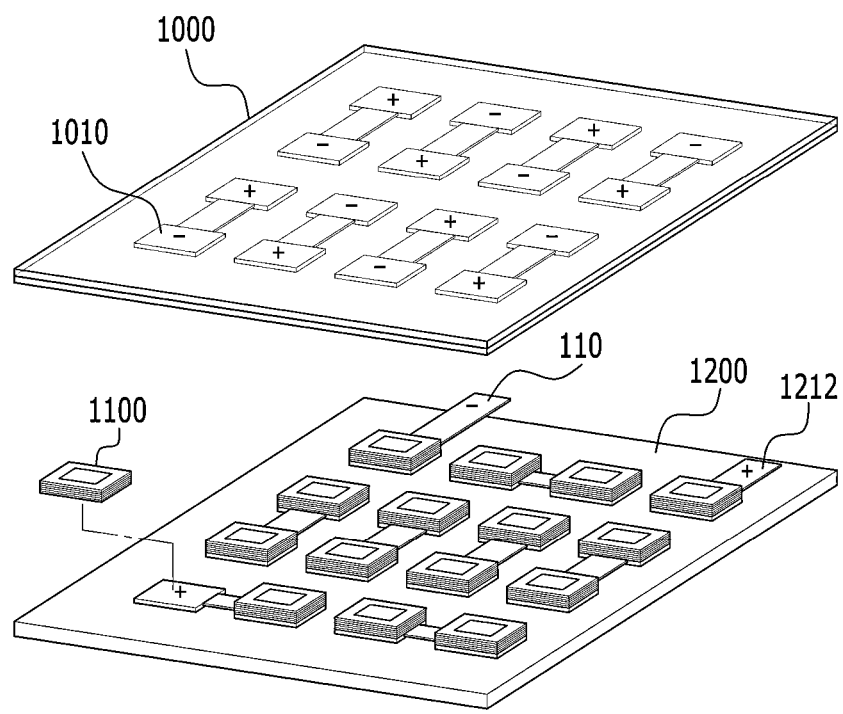
FIG. 9 is a perspective view of the first reverse electrodialysis device according to the exemplary embodiment of the present invention.
Figure 10:
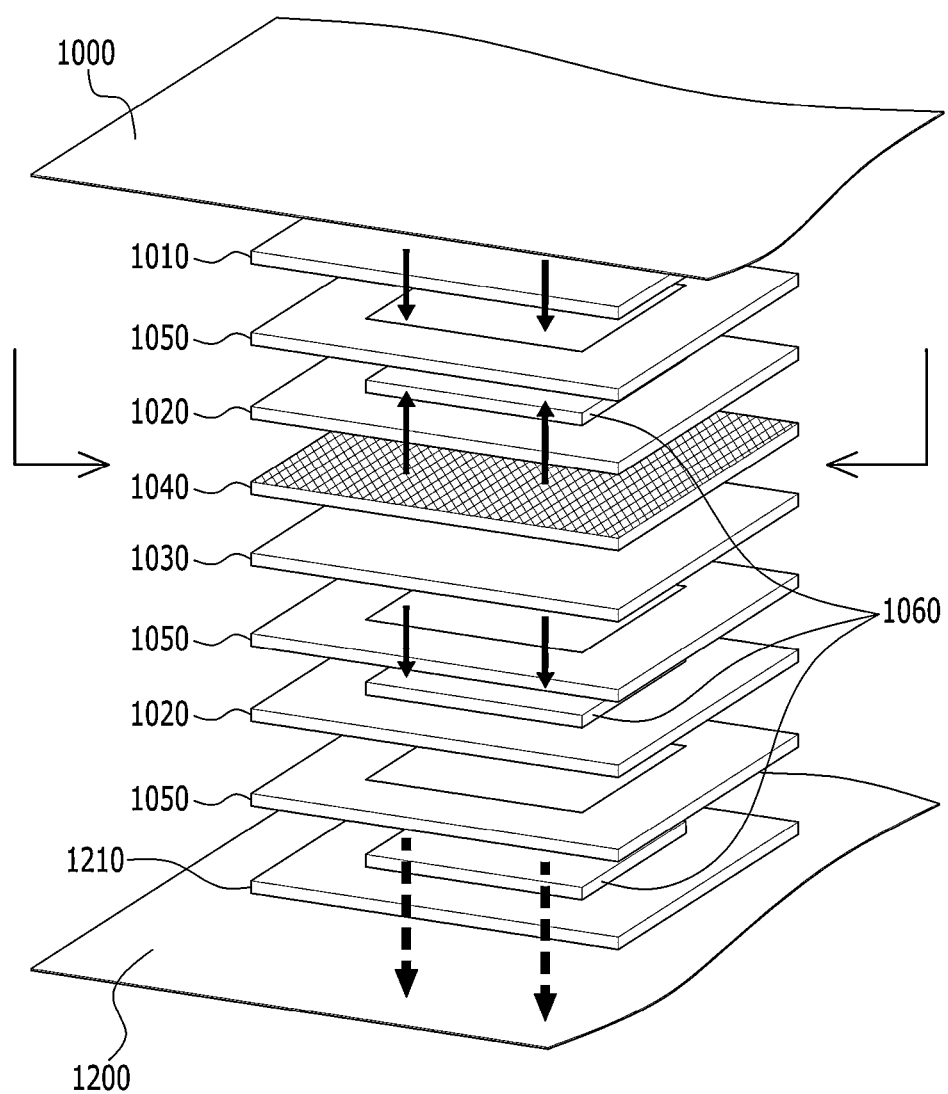
FIG. 10 is an exploded perspective view of a unit cell of a first reverse electrodialysis device according to the exemplary embodiment of the present invention.
Figure 11:
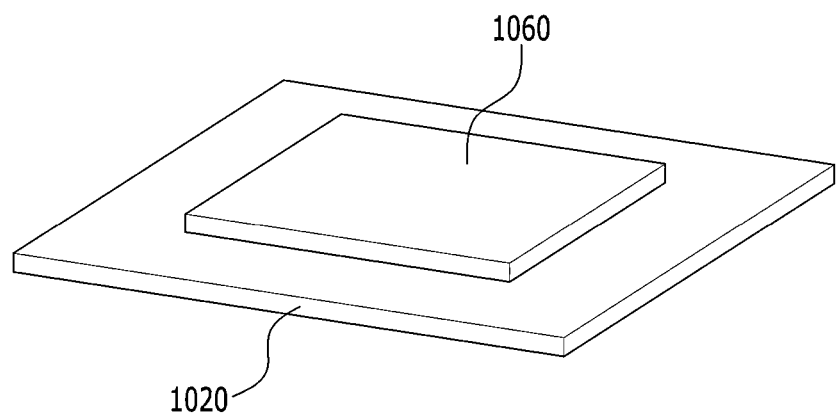
FIG. 11 is a perspective view of an ion exchange membrane used in the reverse electrodialysis device according to the exemplary embodiment of the present invention.
Figure 12:
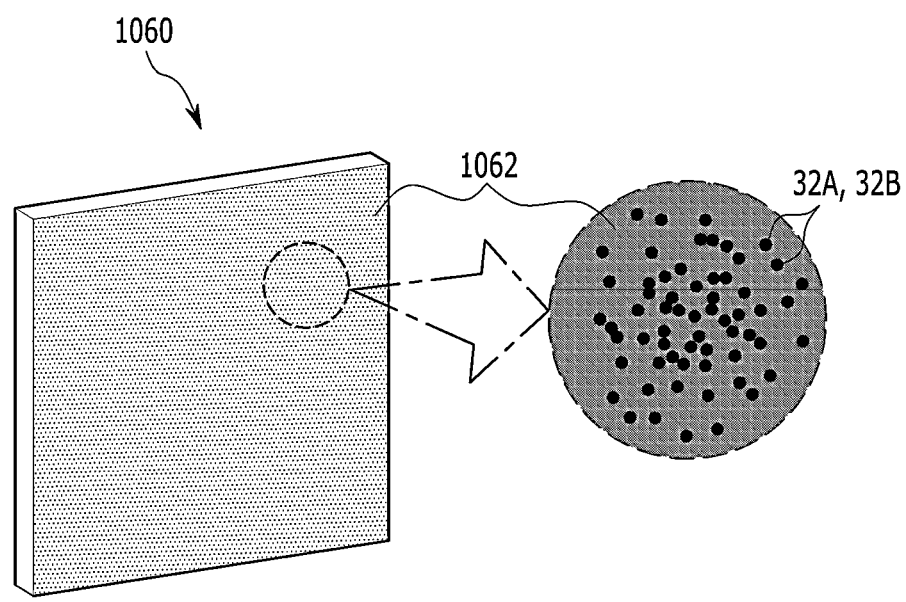
FIG. 12 is a schematic diagram illustrating a result after a useful material is mixed in a porous material and then is patterned.

FIG. 7 is an exploded perspective view of a part of the first electricity generation and nutrient and/or drug delivery module before the bio-signal measurement sensor unit according to the exemplary embodiment of the present invention. FIG. 8 is a perspective view of an electrode layer of a first reverse electrodialysis device according to the exemplary embodiment of the present invention. FIG. 9 is a perspective view of the first reverse electrodialysis device according to the exemplary embodiment of the present invention. FIG. 10 is an exploded perspective view of a unit cell of a first reverse electrodialysis device according to the exemplary embodiment of the present invention. FIG. 11 is a perspective view of a cation-exchange membrane an anion-exchange membrane used in the reverse electrodialysis device according to the exemplary embodiment of the present invention. FIG. 12 is a schematic diagram illustrating a result after a useful material is mixed in a porous material and then is patterned.

Referring to FIGS. 7 to 12, the first electricity generation and nutrient and/or drug delivery module 100 includes a first reverse electrodialysis device 120 and a skin contact delivery unit 150 under the first reverse electrodialysis device 120, and a protection and water supply unit 160 on the first reverse electrodialysis device 120. The lower skin contact delivery unit 150 and the upper protection and water supply unit 160 are in the form of gauze, a hydrogel film, a parafilm, and nonwovens, and include a biocompatible material. When water is supplied to the upper protection and water supply unit 160, water is supplied to the lower first reverse electrodialysis device 120. When water is supplied, ionic nutrients and/or drugs included in each unit cell 1110 of the first reverse electrodialysis device 120 act a high-concentration electrolyte, so that electricity is generated in the first reverse electrodialysis device 120 and mixed water of water and the nutrients and/or drugs is discharged. The discharged mixed water of water and the nutrients and/or drugs directly moves to the skin 10 through the lower skin contact delivery unit 150. A voltage applied from the first reverse electrodialysis device 120 to the skin layer may be varied according to a configuration of the electrode of the first reverse electrodialysis device, and for example, in the case of a positive (+) voltage, when the drug attached to the lower skin contact delivery unit 150 is positively charged in an aqueous solution, the drug may be more effectively delivered deeper into the skin 10.

The skin contact delivery unit may further include nutrients and/or drugs that are not suitable for use as a high-concentration electrolyte of the first reverse electrodialysis device 120 but need to be delivered to the skin layer, and the nutrients and/or drugs may be supplied to the skin 10 together with the mixed water of water and the nutrients and/or drugs discharged through the first reverse electrodialysis device 120.

Referring to FIGS. 8 and 9, the first reverse electrodialysis device 120 has a structure in which a first electrode pattern 1010 is formed in a pad supporting body 1000 and a second electrode pattern 1210 is formed on another pad supporting body 1200, and a plurality of unit cells 1100 of the first reverse electrodialysis device 120 is connected on the patterns. The surface characteristics of the pad supporting bodies 1000 and 1200 may be formed of a hydrophilic property, a hydrophobic property, or a combination of a hydrophilic property and a hydrophobic property in order to maximize the configuration of the electrode and the effect of the electricity generation.

FIG. 9 illustrates the case where the unit cells 1100 are serially connected, but it is a matter of course that the unit cells 1100 are connected in parallel by modifying the first and second electrode patterns 1010 and 1210 of FIG. 8. Further, depending on the case, in order to control the amount of nutrients or drugs supplied and control the amount of power generated, the reverse electrodialysis pad may also be configured by using one unit cell as a matter of course. The first and second electrode patterns 1010 and 1210 may be implemented in a thin film pattern in various schemes, such as 3D printing, screen printing, and casting. However, the forms of FIGS. 8 and 9 are merely the exemplary embodiments of the present invention, and the configurations of the electrode and the unit cell may be modified and applied in various forms in consideration of the smoothness of water supply from the upper protection and water supplying unit 160 and stability of power generation. In FIG. 9, non-described reference numeral 1212 is a terminal for applying polarity (for example, + polarity) to the lower skin contact delivery unit 150. Accordingly, in the case of the first electricity generation and nutrient and/or drug delivery module 100, when the nutrients and/or drugs included in the lower skin contact delivery unit 150 are the positively charged materials in the aqueous solution, the efficiency of the delivery of the nutrients and/or drugs to the skin may be further improved. Referring to FIG. 10, each of the unit cells 1100 of the first reverse electrodialysis device 120 includes a cell stack in which the cation-exchange membranes 1020 and the anion-exchange membrane 1030 are alternately arranged, and electrodes (an oxide electrode and a reduction electrode) 1010 and 1210 disposed at both ends of the cell stack. Gaskets 1050 are disposed between the membranes and between the membrane and the electrode to prevent water and the nutrients within the unit cell 1100 from leaking to the outside. The gasket 1050 may be formed of paraffin, a tape, a nonwoven fabric, an adhesive, and the like in order to enable effective sealing and to flexibly implement the unit cell 110 at the same time, and may be integrated with the ion exchange membrane. Further, a flow path of fresh water (for example, water) is provided between the cation-exchange membrane 1020 and the anion-exchange membrane 1030, and a flow path structure for maintaining a distance between the cation-exchange membrane 1020 and the anion-exchange membrane 1030 may be provided. The provided flow path structure may be a spacer 1040 or a directly patterned channel structure. The ion exchange membranes 1020 and 1030, the gasket 1050, the flow path structure (for example, the spacer) 1040, and the like configuring the unit cell may be made of a biocompatible material. In FIG. 10, left and right arrows represent the supply of water, and solid lines represent the movements of ionic nutrients and/or drugs and water through the ion exchange membranes 1020 and 1030. Dotted lines represent the mixed water of water and the nutrients and/or drugs discharged through the unit cell 1100 of the first reverse electrodialysis device 120. Referring to FIGS. 11 and 12, a porous pattern 1060 including nutrients may be formed on a surface of the ion exchange membrane 1020. In the porous pattern 1060, nutrients 32A and 32B dispersedly exist in a porous region in a porous material layer 1062. As long as a material is capable of providing a pore size through which the nutrients and/or drugs 32A and 32B are inserted, such as hydrogel, a carbon porous material, a porous polymer, porous ceramic, porous metal, or porous silica, the material is applicable to the porous material layer 1062. The porous polymer may include a natural polymer, such as chitosan, alginic acid, collagen, and haialonic acid. More preferably, a material capable of providing flexibility and biocompatibility is more preferable. In the present invention, the porous material may be a key component capable of acting as a pump in the subminiature salinity gradient power generation technology. More particularly, a pore size of the porous material adjusts the amount of inserted nutrients and/or drugs 32A and 32B that are in contact with the water supplied from the upper protection and water supply unit 160 and discharged to be uniformly maintained to act as a sort of pump which is capable of controlling the amount moved through the ion exchange membrane 1020. This means the uniform maintenance of the amount of power generated in the small or subminiature salinity gradient power generation technology aspect, and may serve to stably supply nutrients and/or drugs to skin and stably maintain the driving of the sensor and the transmission of the signal. The nutrients and/or drugs 32A and 32B may include vitamins, nutritional fluids, skin regenerating agents, heart rate regulating drugs, thermoregulation agents, anti-inflammatory agents, blood pressure regulating drugs, bone regenerative drugs, blood sugar regulating drugs, neuroregenerating agents, ionized nutrients, various bioactive substances that are complexes thereof, or the like which need to be provided to the body. Further, when the bio-signal measured by the bio-signal measurement sensor unit 300 is related to a disease, the nutrients and/or drugs 32A and 32B may also include drugs. For example, when the bio-signal measured by the bio-signal measurement sensor unit 300 is related to a heart rate, the nutrients and/or drugs 32A and 32B may be drugs for adjusting a heart rate, when the bio-signal measured by the bio-signal measurement sensor unit 300 is related to a body temperature, the nutrients and/or drugs 32A and 32B may be thermoregulation agents, such as a fever reducer, and when the bio-signal measured by the bio-signal measurement sensor unit 300 is related to high blood pressure and the like, the nutrients and/or drugs 32A and 32B may be a blood pressure lowering agent or a blood pressure booster.

The foregoing materials are merely the examples, and various materials may be applied as a matter of course. The porous pattern 1060 including the nutrients and/or drugs may implement the porous material and the mixture of the nutrients and/or drug in the form of a thin film and various shapes of patterns by various methods, such as 3D printing, screen printing, and casting. Like the present exemplary embodiment, the porous pattern 1060 may also be formed on the anion-exchange membrane 1030, as well as the cation-exchange membrane 1020, and may also be formed on both the cation-exchange membrane and the anion-exchange membrane as a matter of course.

When water is supplied to the unit cell 1100 of the first reverse electrodialysis device 120 through the upper protection and water supply unit 160, water is supplied in a down direction from the upper electrode 1010 and a lateral surface of the unit cell 1100 of the first reverse electrodialysis device 120, and water flows along the spacer 1040 for each unit cell 1100 of the first reverse electrodialysis device 120. By the flowing water, the nutrients 32A and 32B are eluted and flow out from the porous pattern 1060 including the nutrients and/or drugs formed on the adjacent ion exchange membrane 1020. The eluted and flowing-out nutrients and/or drugs act as an electrolyte, so that the anions move toward the anion-exchange membrane 1030 and the cations move toward the cation-exchange membrane 1020 to generate a potential difference, and electrons flow by an oxidation-reduction reaction on the first electrode pattern 1010 and second electrode pattern 1210 to generate electricity. Further, the mixed water of the nutrients and/or drugs and water is discharged as effluent water. In order to enable water to be supplied in the down direction from the upper electrode 1010, the upper electrode 1010 may be formed with a pattern which is capable of providing a flow path of water.

In order to allow the mixed water of the nutrients and/or drug and the water to be discharged well to the outside and increase the amount of diluted nutrients and/or drugs, the electrode 1210 may include the porous pattern 1060 including the nutrients and/or drugs desired to be finally delivered to the skin thereon.

The nutrients and/or drugs discharged toward the skin are discharged in a diluted state. Accordingly, as illustrated in FIG. 7, the first electricity generation and nutrient and/or drug delivery module 100 generates electricity and deliver the diluted nutrients and/or drugs to the skin.

Figure 13:
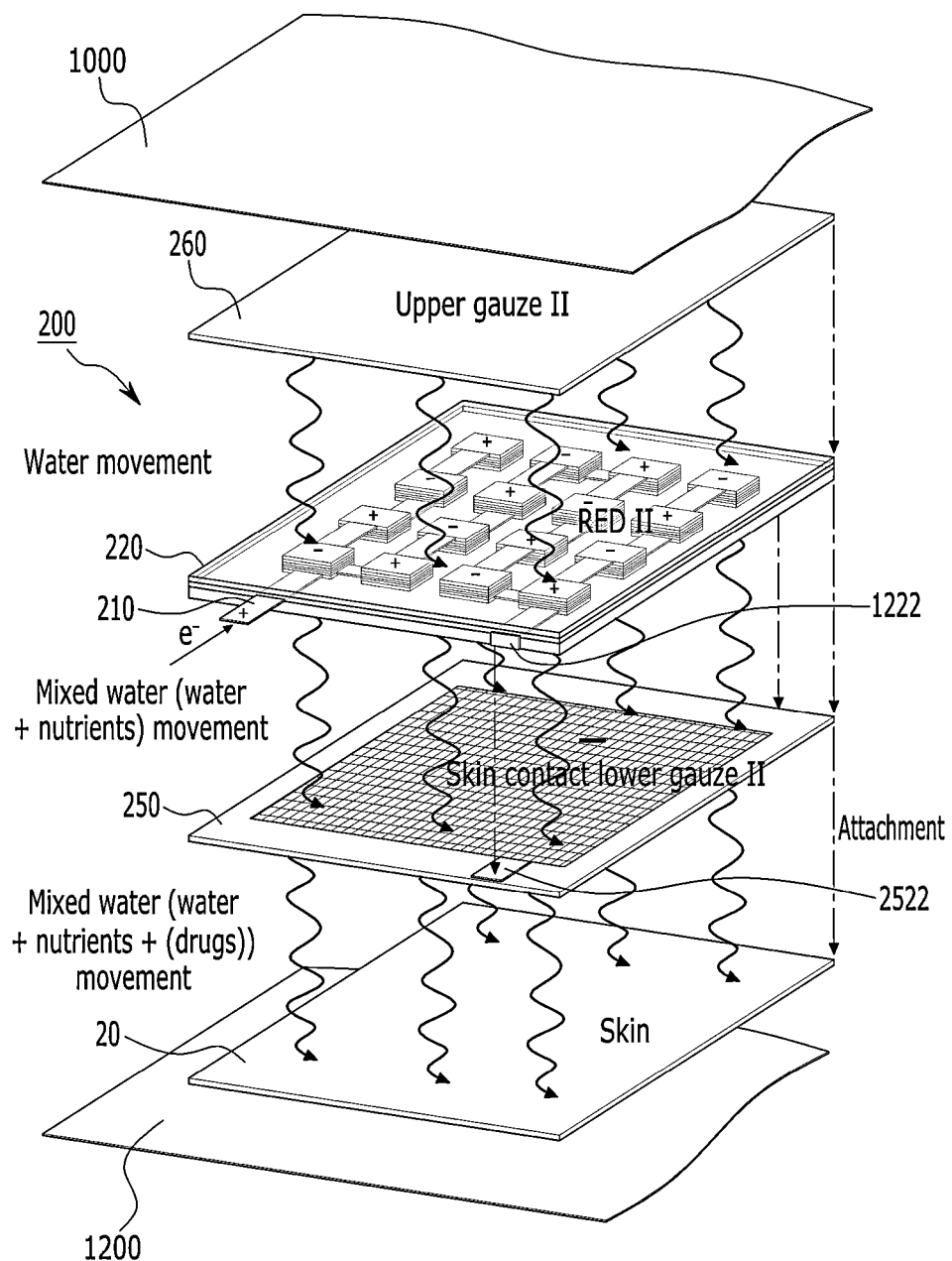
FIG. 13 is an exploded perspective view of a second electricity generation and nutrient and/or drug delivery module according to the exemplary embodiment of the present invention.
Figure 14:
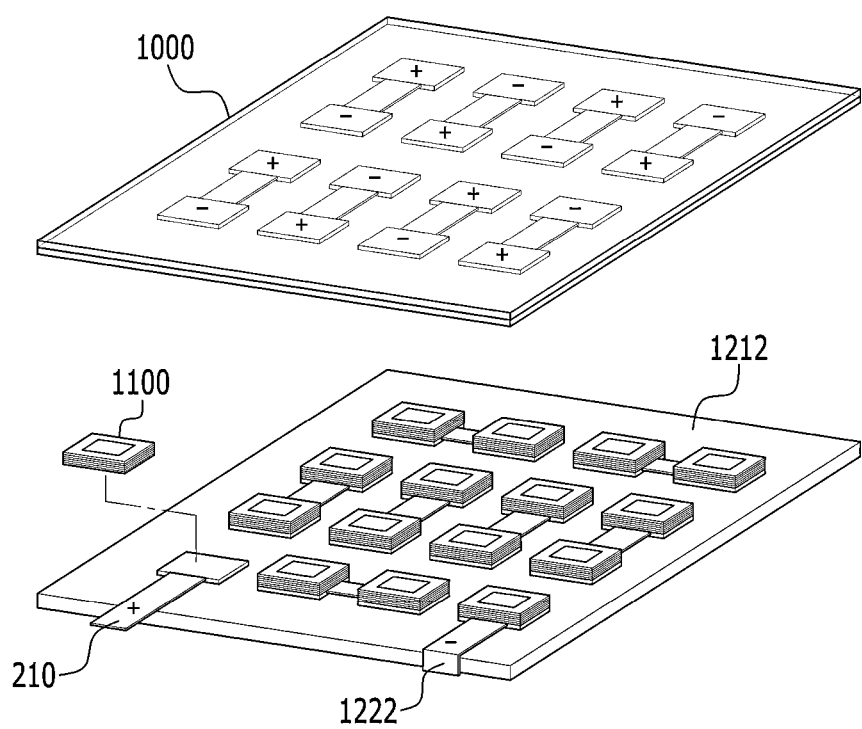
FIG. 14 is a perspective view of the second reverse electrodialysis device according to the exemplary embodiment of the present invention.

FIG. 13 is an exploded perspective view of the second electricity generation and nutrient and/or drug delivery module 200 according to the exemplary embodiment of the present invention, and FIG. 14 is a perspective view of the second reverse electrodialysis device 220 according to the exemplary embodiment of the present invention.

The second electricity generation and nutrient and/or drug delivery module 200 has the same basic structure as the first electricity generation and nutrient and/or drug delivery module 100 illustrated in FIG. 7. There is a difference in that when the external terminal 110 to be connected to the bio-signal measurement sensor unit 300 discharged to the outside in the first reverse electrodialysis device 120 (see FIG. 7) is a negative pole, the external terminal 210 which is exposed to the outside from the second reverse electrodialysis device 220 to be connected to the bio-signal measurement sensor unit 300 is a positive pole. Further, another terminal 1222 may be a terminal for applying polarity (for example, negative (−) polarity) to the lower skin contact delivery unit 250. As a result, when the nutrients and/or drugs included in the lower skin contact delivery unit 250 is the negatively charged materials in the aqueous solution, the efficiency of delivering the nutrients and/or drugs to the skin may be further improved.

Figure 15:
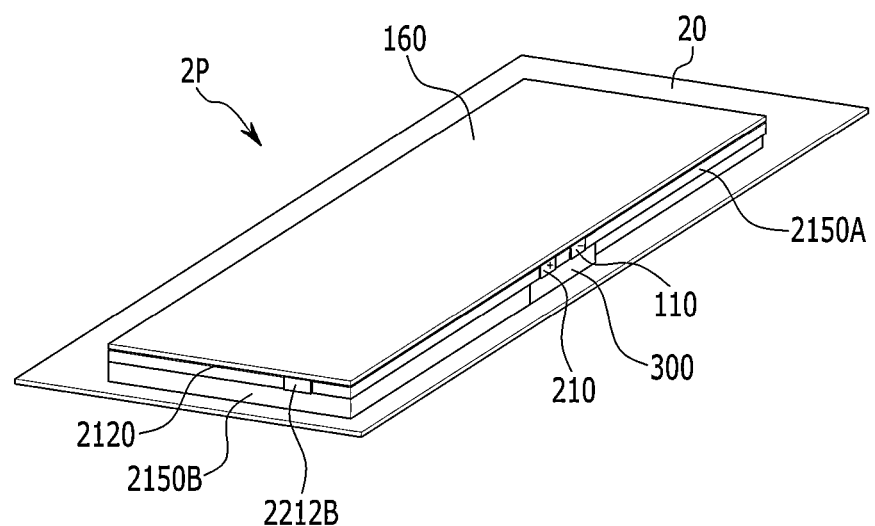
FIG. 15 is a perspective view of a patch before an energy self-sufficient real time bio-signal monitoring and nutrient delivery system is attached to skin according to another exemplary embodiment of the present invention.
Figure 16:
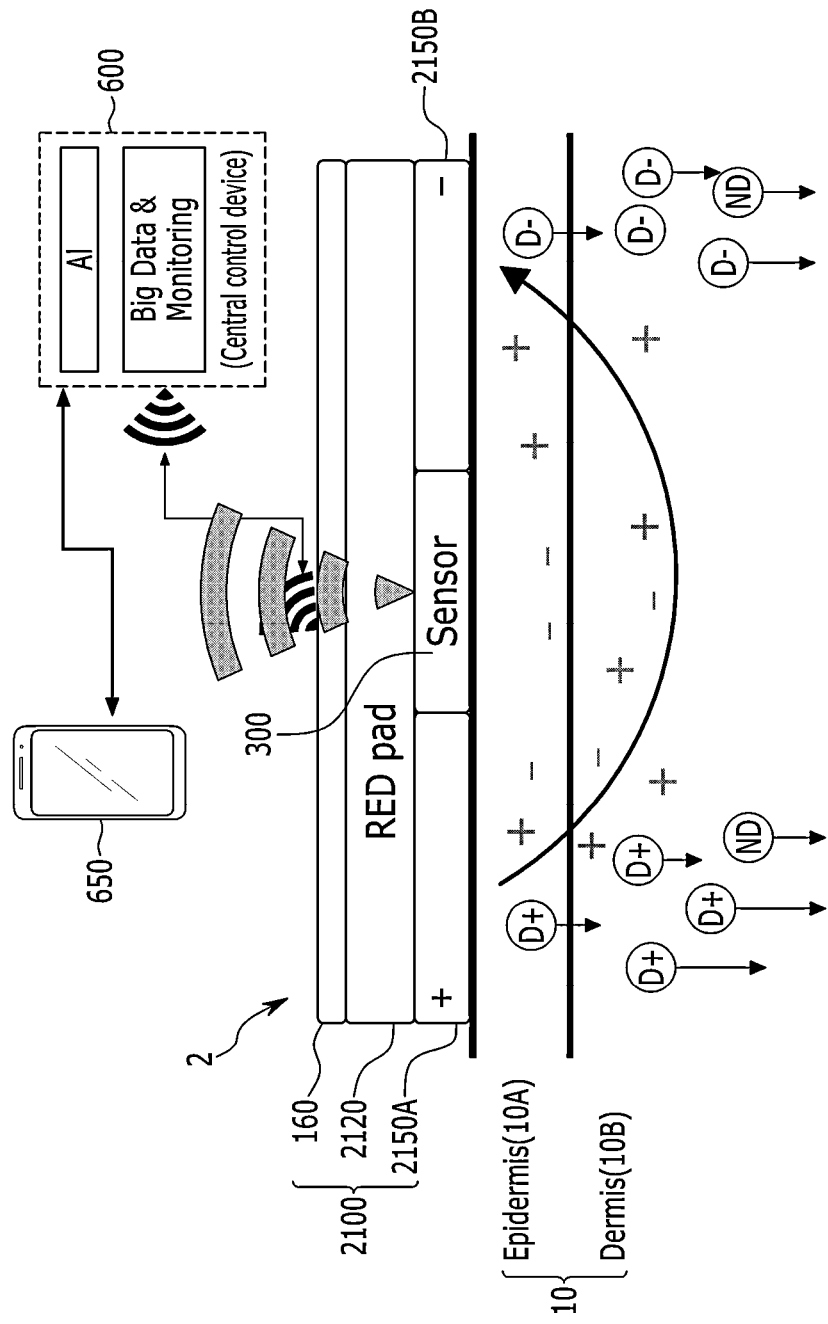
FIG. 16 is a cross-sectional view of the case where the energy self-sufficient real time bio-signal monitoring and nutrient delivery system is attached to skin with a removal of an attachment pad according to another exemplary embodiment of the present invention.
Figure 17:
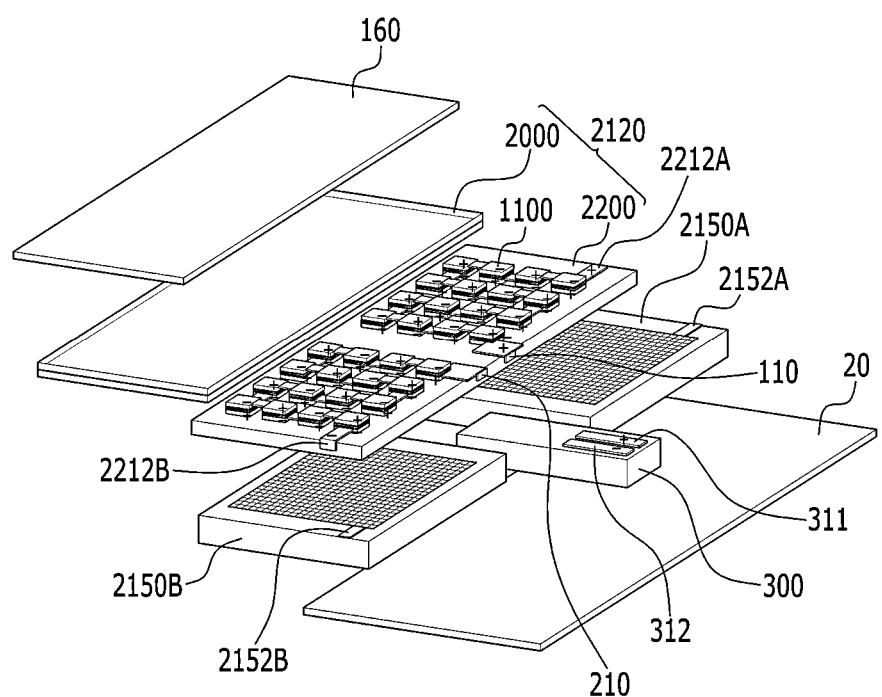
FIG. 17 is an exploded perspective view of the energy self-sufficient real time bio-signal monitoring and nutrient delivery system according to another exemplary embodiment of the present invention.

FIG. 15 is a perspective view of a patch before an energy self-sufficient real time bio-signal monitoring and nutrient delivery system is attached to skin according to another exemplary embodiment of the present invention. FIG. 16 is a cross-sectional view of the case where the energy self-sufficient real time bio-signal monitoring and nutrient delivery system is attached to skin with a removal of an attachment pad according to another exemplary embodiment of the present invention. FIG. 17 is an exploded perspective view of the energy self-sufficient real time bio-signal monitoring and nutrient delivery system according to another exemplary embodiment of the present invention.

Referring to FIGS. 15 to 17, a patch 2P is preserved or stored in the form in which the energy self-sufficient real time bio-signal monitoring and nutrient delivery system 2 is attached onto an attachment pad 20. Although not illustrated in the drawing, a pad (not illustrated) that is detachable just before the use may also be further included on the energy self-sufficient real time bio-signal monitoring and nutrient delivery system 2. The system 2 includes an electricity generation and nutrient and/or drug delivery module 2100 for supplying electricity for energy self-sufficiency and simultaneously supplying useful materials 32 to skin 10, a bio-signal measurement sensor unit 300 for monitoring a bio-signal in real time, and a central control device 600.

Unlike the exemplary embodiment, the energy self-sufficient real time bio-signal monitoring and nutrient delivery system 2 according to another exemplary embodiment of the present invention includes one electricity generation and nutrient and/or drug delivery module 2100. Accordingly, only one protection and water supply unit 160 is installed in an upper portion of the electricity generation and nutrient and/or drug delivery module 2100, but first and second skin contact delivery units 2150A and 2150B to which voltages having different polarity are applied are included in a lower portion of the electricity generation and nutrient and/or drug delivery module 2100.

The electricity generation and nutrient and/or drug delivery module 2100 is electrically connected with external input terminals 311 and 312 of the bio-signal measurement sensor unit 300 through external input terminals 2210A and 2210B, respectively. Further, the electricity generation and nutrient and/or drug delivery module 2100 applies voltages of different polarity to terminals 2152A and 2152B of the first and second skin contact delivery units 2150A and 2150B through external input terminals 2212A and 2212B, respectively. The amount of nutrients and/or drugs delivered through epidermis 10A and dermis 10B may be adjusted according to sizes of currents and voltages supplied through the electricity generation and nutrient and/or drug delivery module 2100.

Like the exemplary embodiment of FIGS. 15 to 17, when the system includes one electricity generation and nutrient and/or drug delivery module 2100, there is an advantage in that it is possible to easily manufacture the system and simplify the system, and easily combine the electricity generation and nutrient and/or drug delivery module 2100 and the sensor.

Figure 18:
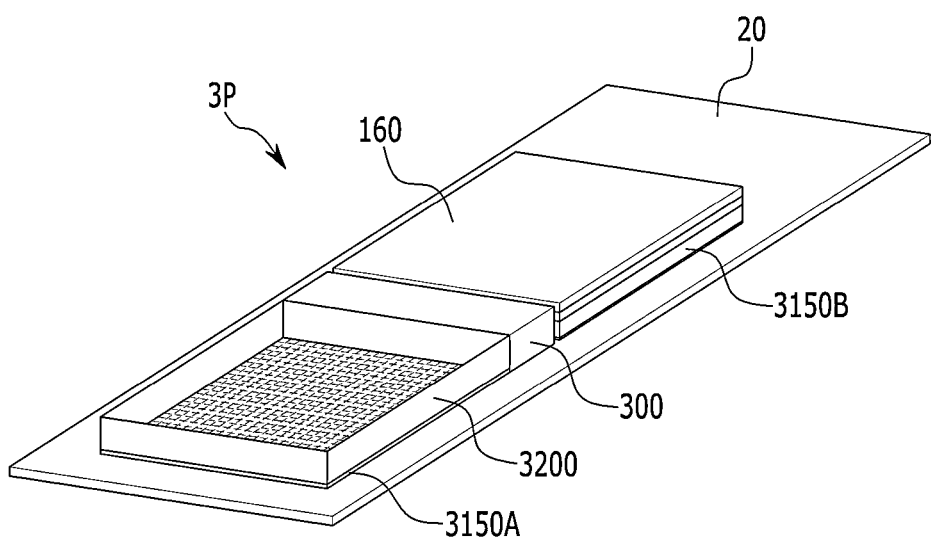
FIG. 18 is a perspective view of a patch before an energy self-sufficient real time bio-signal monitoring and nutrient delivery system is attached to skin according to still another exemplary embodiment of the present invention.
Figure 19:
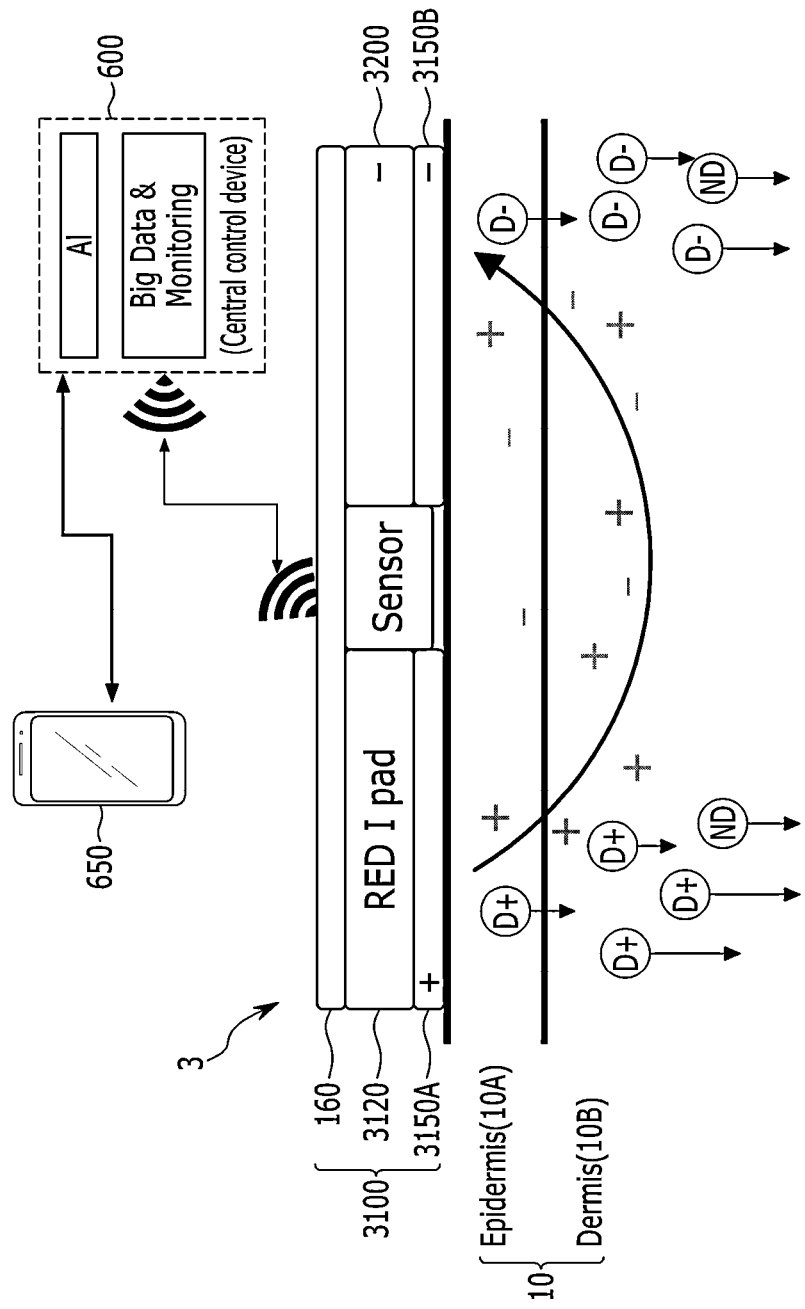
FIG. 19 is a cross-sectional view of the case where the energy self-sufficient real time bio-signal monitoring and nutrient delivery system is attached to skin with a removal of an attachment pad according to still another exemplary embodiment of the present invention.
Figure 20:
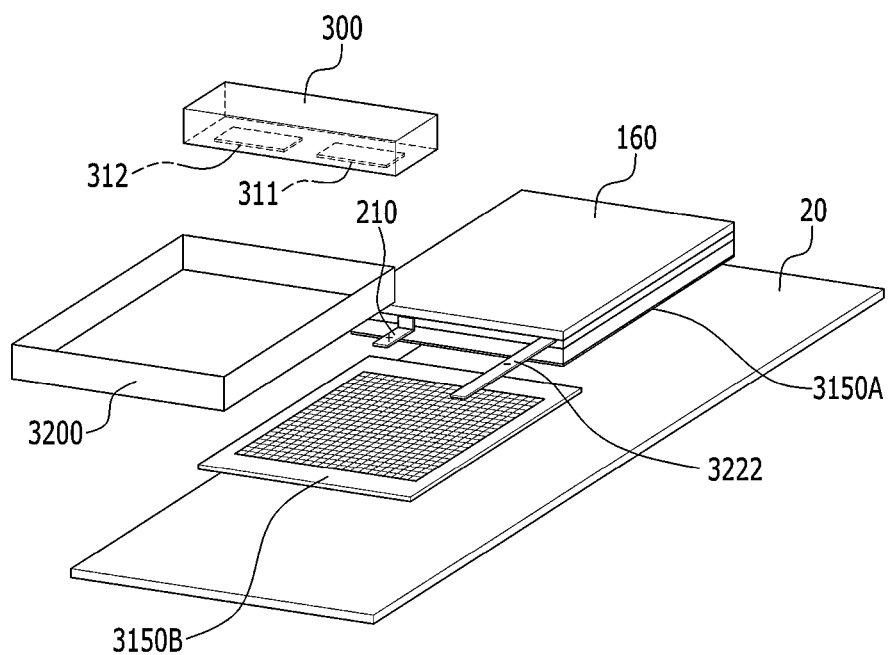
FIG. 20 is an exploded perspective view of an energy self-sufficient real time bio-signal monitoring and nutrient delivery system according to still another exemplary embodiment of the present invention.

FIG. 18 is a perspective view of a patch before an energy self-sufficient real time bio-signal monitoring and nutrient delivery system is attached to skin according to still another exemplary embodiment of the present invention. FIG. 19 is a cross-sectional view of the case where the energy self-sufficient real time bio-signal monitoring and nutrient delivery system is attached to skin with a removal of an attachment pad according to still another exemplary embodiment of the present invention. FIG. 20 is an exploded perspective view of an energy self-sufficient real time bio-signal monitoring and nutrient delivery system according to still another exemplary embodiment of the present invention.

Referring to FIGS. 18 to 20, a patch 3P is preserved or stored in the form in which the energy self-sufficient real time bio-signal monitoring and nutrient delivery system 3 is attached onto an attachment pad 20. Although not illustrated in the drawing, a pad (not illustrated) that is detachable just before the use may also be further included on the energy self-sufficient real time bio-signal monitoring and nutrient delivery system 2. The system 3 includes an electricity generation and nutrient and/or drug delivery module 3100 for supplying electricity for energy self-sufficiency and simultaneously supplying nutrients and/or drugs to skin 10, a bio-signal measurement sensor unit 300 for monitoring a bio-signal in real time, and a central control device 600.

Unlike the foregoing exemplary embodiments, the energy self-sufficient real time bio-signal monitoring and nutrient delivery system 3 according to still another exemplary embodiment of the present invention includes the electricity generation and nutrient and/or drug delivery module 3100 only in a partial region of the system 3 and includes electrodes 3200 for delivering nutrients in the remaining regions. First and second skin contact delivery units 3150A and 3150B applying voltages of different polarity are included under the electricity generation and nutrient and/or drug delivery module 3100 and the electrode 3200, respectively. A protection and water supply unit 160 is installed in an upper portion of the electricity generation and nutrient and/or drug delivery module 3100.

The electricity generation and nutrient and/or drug delivery module 3100 is electrically connected with external input terminals 311 and 312 of the bio-signal measurement sensor unit 300 through external input terminals 210 and 3222, respectively. Further, one of the external input terminals 3222 is extended and connected up to the second skin contact delivery unit 3150B under the electrode 3200. The amount of nutrients and/or drugs delivered through epidermis 10A and dermis 10B may be adjusted according to sizes of currents and voltages supplied through the electricity generation and nutrient and/or drug delivery module 3100.

Figure 21:
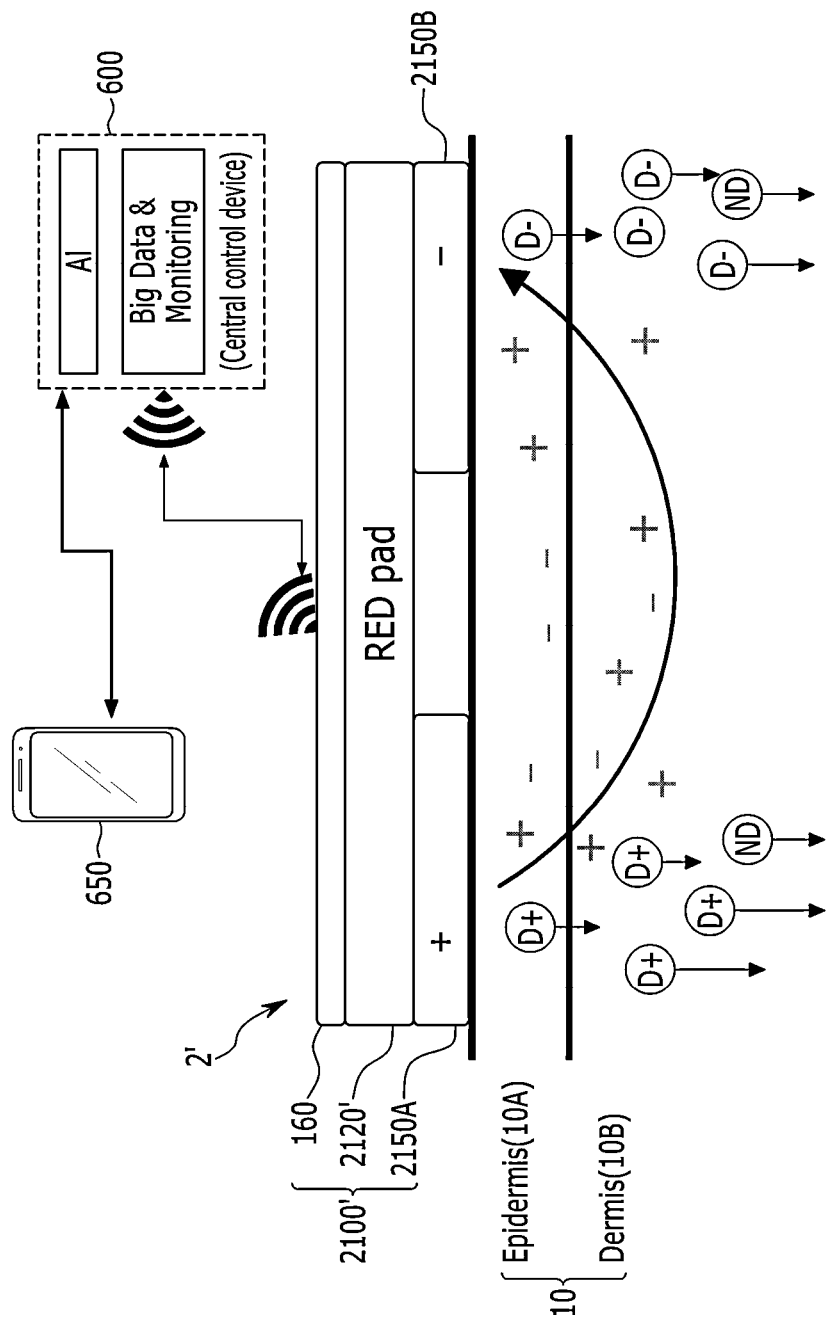
FIG. 21 is a diagram illustrating a cross-section of an iontophoresis module for delivering nutrients according to an exemplary embodiment of the present invention.
Figure 22:
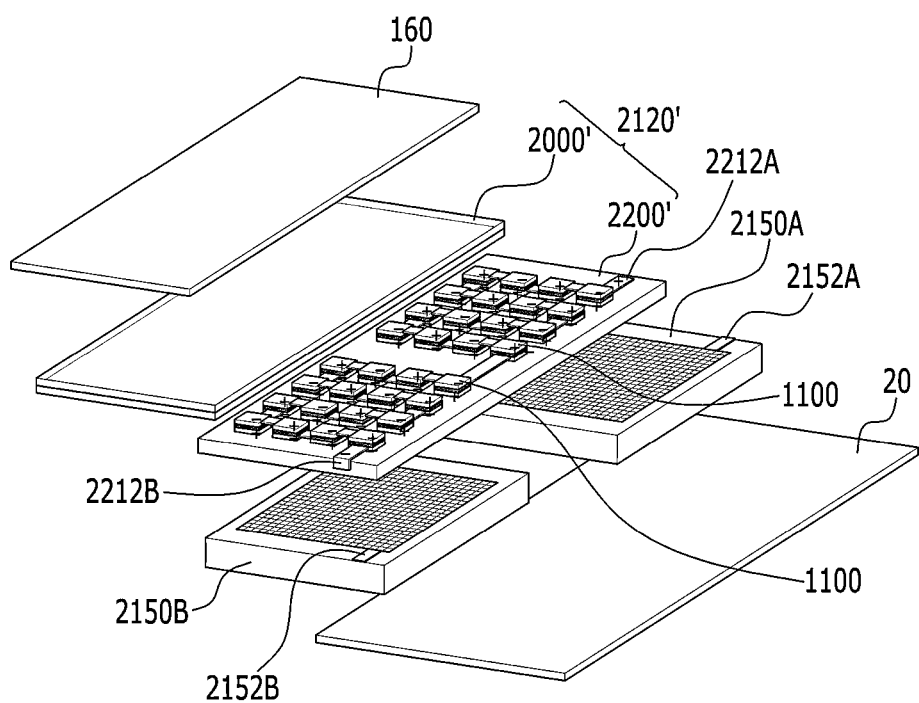
FIG. 22 is an exploded perspective view of the iontophoresis module for delivering nutrients according to the exemplary embodiment of the present invention.

FIG. 21 is a diagram illustrating a cross-section of an iontophoresis module 2' for delivering nutrients according to an exemplary embodiment of the present invention. FIG. 22 is an exploded perspective view of the iontophoresis module 2' for delivering nutrients.

Referring to FIGS. 21 and 22, the iontophoresis module 2' for delivering nutrients has a structure including no bio-signal measurement sensor unit 300 (see FIG. 16) unlike the energy self-sufficient real time bio-signal monitoring and nutrient delivery system 2 described with reference to FIGS. 15 to 17. Accordingly, the terminals 2210A and 2210B (see FIG. 17) for supply power sources to the bio-signal measurement sensor unit 300 (see FIG. 17) are not included in a reverse electrodialysis device 2120', and the adjacent reverse electrodialysis unit cells 1100 are connected with each other.

Further, the external input terminals 2212A and 2212B of the reverse electrodialysis device 2120' configuring the iontophoresis module 2' for delivering nutrients apply voltages of different polarity to terminals 2152A and 2152B of the lower first and second skin contact delivery units 2150A and 2150B, respectively.

Accordingly, as illustrated in FIG. 21, when water is supplied through the upper protection and water supply unit 160 after the system is attached to the skin, the water is supplied to the lower reverse electrodialysis device 2120'. When water is supplied, water is supplied to the flow path structure (see the spacer 1040 of FIG. 10) of each unit cell 1100 (see FIG. 17) of the reverse electrodialysis device 2120', the water permeates into the porous pattern 1060 (see FIG. 10) on the surface of the adjacent cation-exchange membrane 1020 (see FIG. 10), and the ionic nutrients and/or drugs included in the porous pattern 1060 (see FIG. 10) act as a high-concentration electrolyte, so that electricity is generated in the reverse electrodialysis device 2120' and simultaneously the mixed water of the water and the nutrients and drugs is discharged. The discharged mixed water of water and the nutrients directly moves to the skin 10 through the lower first and second skin contact delivery units 2150A and 2150B. The drugs positively charged or neutrally charged and the drugs negatively charged or neutrally charged may be delivered deeper to the skin 10 through the first skin contact delivery unit 2150A to which a positive (+) voltage is applied and the second skin contact delivery unit 2150B to which a negative (−) voltage is applied, respectively.

The first and second skin contact delivery units 2150A and 2150B may further include nutrients and/or drugs that are not suitable for use as a high-concentration electrolyte of the reverse electrodialysis device 2120' but need to be delivered to the skin layer, and the nutrients and/or drugs may be supplied to the skin 10 together with the mixed water of water and the nutrients and/or drugs discharged through the reverse electrodialysis device 2120'.

Figure 23:
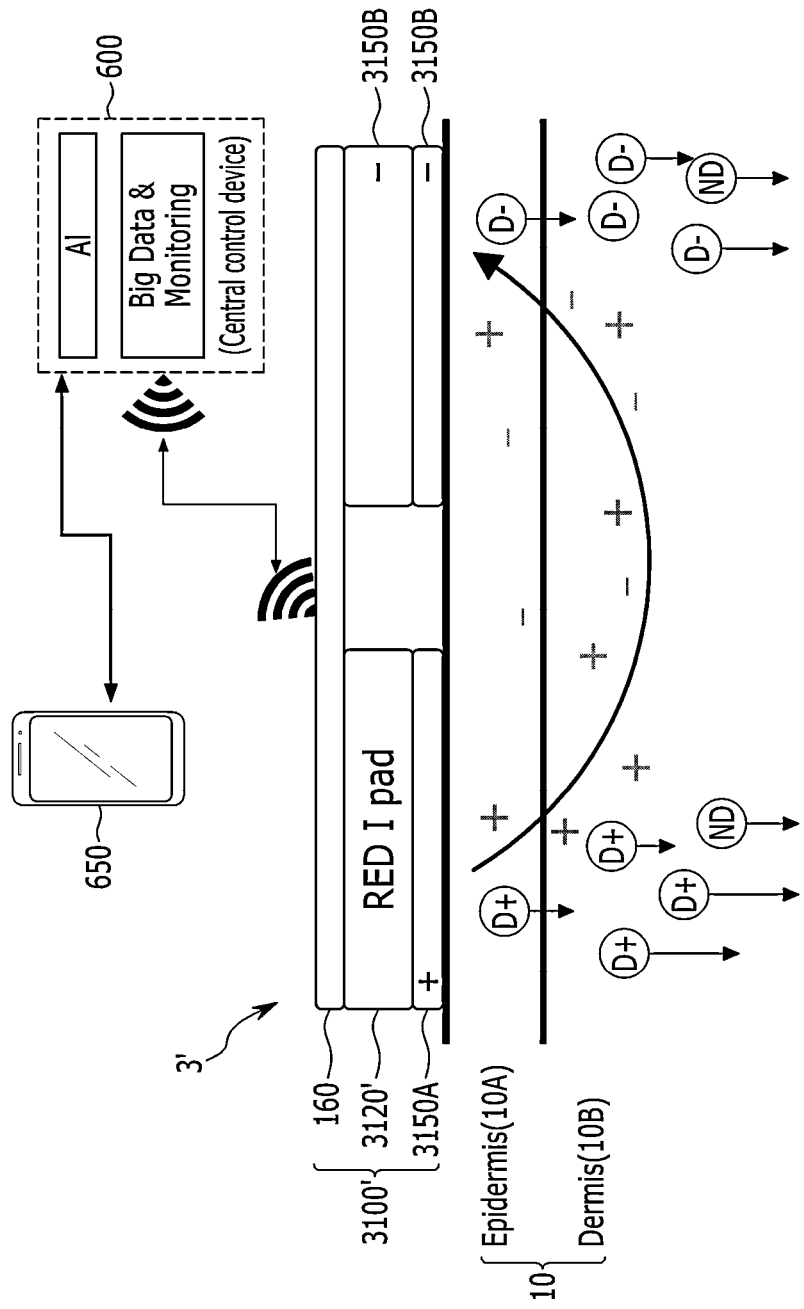
FIG. 23 is a diagram illustrating a cross-section of an iontophoresis module for delivering nutrients according to another exemplary embodiment of the present invention.

FIG. 23 is a diagram illustrating a cross-section of an iontophoresis module 3' for delivering nutrients according to another exemplary embodiment of the present invention.

Referring to FIG. 23, the iontophoresis module 3' for delivering nutrients has a structure including no bio-signal measurement sensor unit 300 (see FIG. 18) unlike the energy self-sufficient real time bio-signal monitoring and nutrient delivery system 2 described with reference to FIGS. 18 to 20, and other remaining constituent elements are substantially the same.

A reverse electrodialysis device 3120' of the iontophoresis module 3' for delivering nutrients applies voltages of different polarity to each of lower first and second skin contact delivery units 3150A and 3150B. Accordingly, as illustrated in FIG. 23, when water is supplied through the upper protection and water supply unit 160 after the system is attached to the skin, the water is supplied to the lower reverse electrodialysis device 3120'. When water is supplied, water is supplied to the flow path structure (see the spacer 1040 of FIG. 10) of each unit cell 1100 (see FIG. 17) of the reverse electrodialysis device 3120', the water permeates into the porous pattern 1060 (see FIG. 10) on the surface of the adjacent cation-exchange membrane 1020 (see FIG. 10), and the ionic nutrients and/or drugs included in the porous pattern 1060 (see FIG. 10) act as a high-concentration electrolyte, so that electricity is generated in the reverse electrodialysis device 3120' and simultaneously the mixed water of the water and the nutrients and drugs is discharged. The discharged mixed water of water and the nutrients directly moves to the skin 10 through the lower first and second skin contact delivery units 3150A and 3150B. The drugs positively charged or neutrally charged and the drugs negatively charged or neutrally charged may be delivered deeper to the skin 10 through the first skin contact delivery unit 3150A to which a positive (+) voltage is applied and the second skin contact delivery unit 3150B to which a negative (−) voltage is applied, respectively.

The first and second skin contact delivery units 3150A and 3150B may further include nutrients and/or drugs that are not suitable for use as a high-concentration electrolyte of the reverse electrodialysis device 3120' but need to be delivered to the skin layer, and the nutrients and/or drugs may be supplied to the skin 10 together with the mixed water of water and the nutrients and/or drugs discharged through the reverse electrodialysis device 3120'.

The following experimental examples and drawings are provided to better understand the conceptual aspects and the method of the exemplary embodiments of the present invention and to further elaborate the operation and the effects. However, the experimental examples are merely the examples of the invention, and the scope of the present invention is not defined by the experimental examples.

Riboflavin Release Test

First, riboflavin and hydrogel were mixed, and the mixture was printed in a predetermined size (5 mm×5 mm×0.2 mm) so that riboflavin per film is 100 μg and was incubated in 24-well plates, each of which is filled with DI of 500 μl, at 37° C. Then, the amount of riboflavin released was measured by an absorbance measurement method at 450 nm for each time zone. The result is illustrated in FIGS. 24 and 25.

Figure 24:
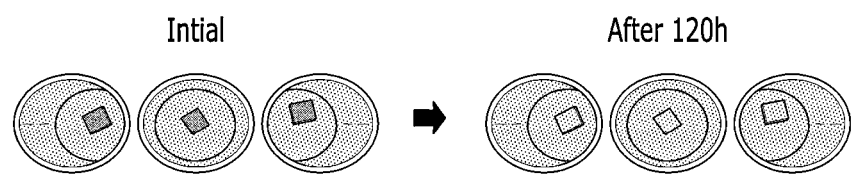
FIG. 24 is an image before and after a riboflavin release test.
Figure 25:
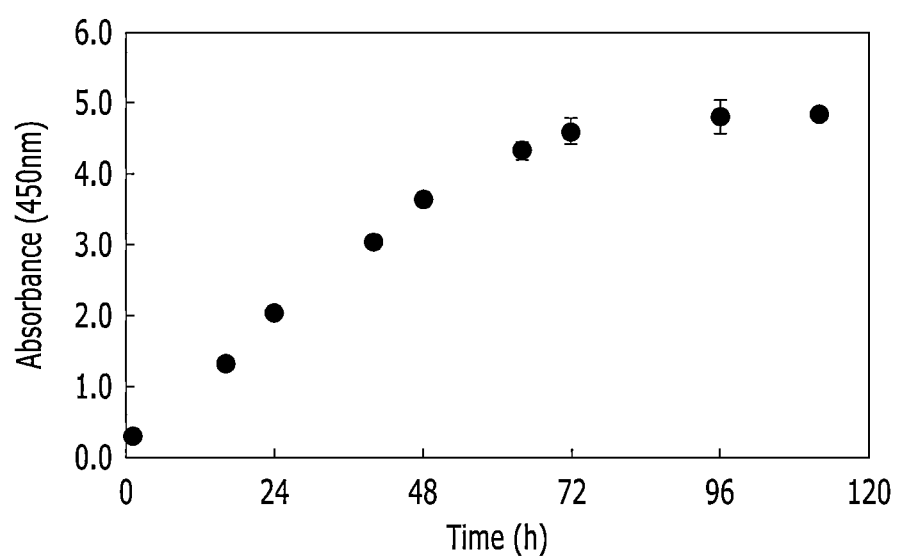
FIG. 25 is a graph illustrating a result of the riboflavin release test.

Referring to the result of FIG. 24, it can be seen that almost all of the riboflavin is released after about 120 h. Then, from the result of FIG. 25, it can be seen that riboflavin is slowly released from hydrogel over time and almost all of the riboflavin is released after a predetermined time (about 72 h). That is, by 72 h, almost the constant amount of riboflavin is supplied to the ion exchange membrane through the porous hydrogel.

Ascorbic Acid Release Test

First, ascorbic acid and hydrogel were mixed, and the mixture was printed in a predetermined size (5 mm×5 mm×0.2 mm) so that ascorbic acid per film is 1 mg and was incubated in 96-well plates, each of which is filled with DI of 50 μl, at 37° C. Then, the amount of ascorbic acid released was measured by α,α-diphenyl-β-picrylhydrazyl (DPPH) assay analysis method for each time zone. The result is illustrated in FIG. 26.

Figure 26:
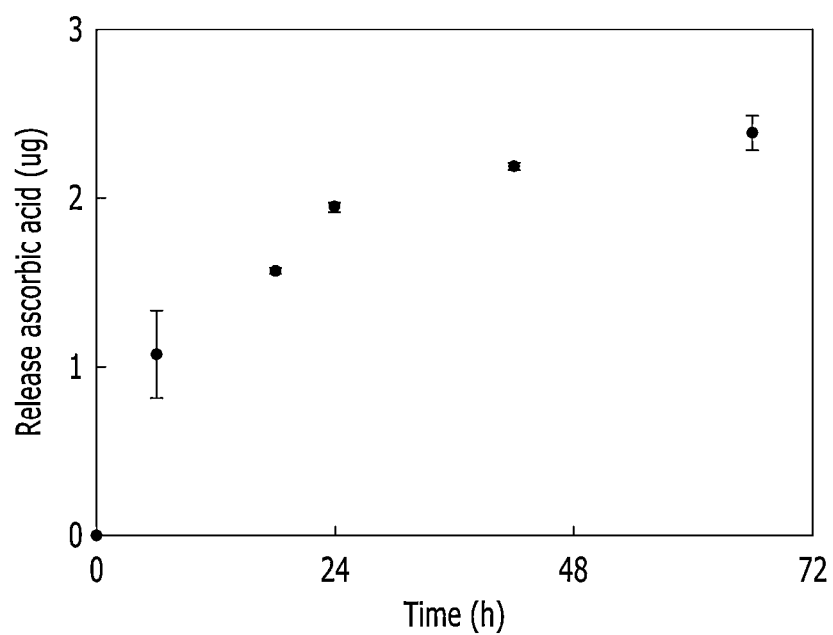
FIG. 26 is a graph illustrating a result of an ascorbic acid release test.

From the result of FIG. 26, it can be seen that ascorbic acid is slowly released over time and almost all of the ascorbic acid is released after a predetermined time (about 72 h).

Electricity Generation Test in Coin Stack

A cell consisting of a cation-exchange membrane and an anion-exchange membrane manufactured by KIER and having a size of 2.7 cm×2.8 cm was formed into 10 stacks, and then an RED coin stack cell was formed by using platinum gauze as an electrode. One cell was formed as a cell having a solid salt layer of vitamins (ascorbic acid) and another cell was formed as a cell having an NaCl solid salt layer, and each cell was immersed in deionized water, and then OCV was measured.

Figure 27:
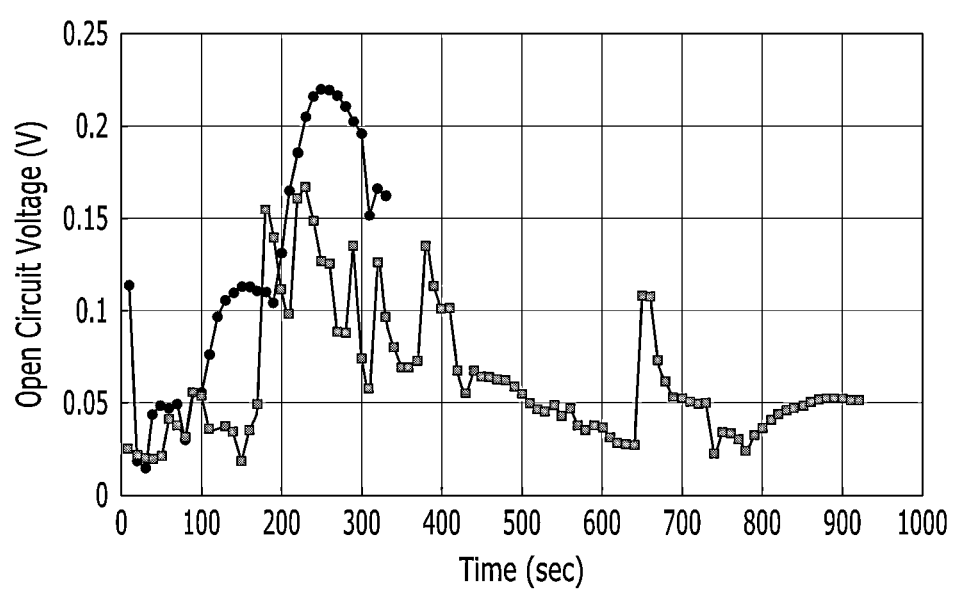
FIG. 27 is an OCV graph measured after an application of vitamin.

The result is illustrated in FIG. 27. From the result of FIG. 27, it can be seen that in the case of using vitamins, after the initial ion exchange membrane swelling time, the OCV was nearly 0.2 V.

Electricity Generation Test in General Stack

Figure 28:
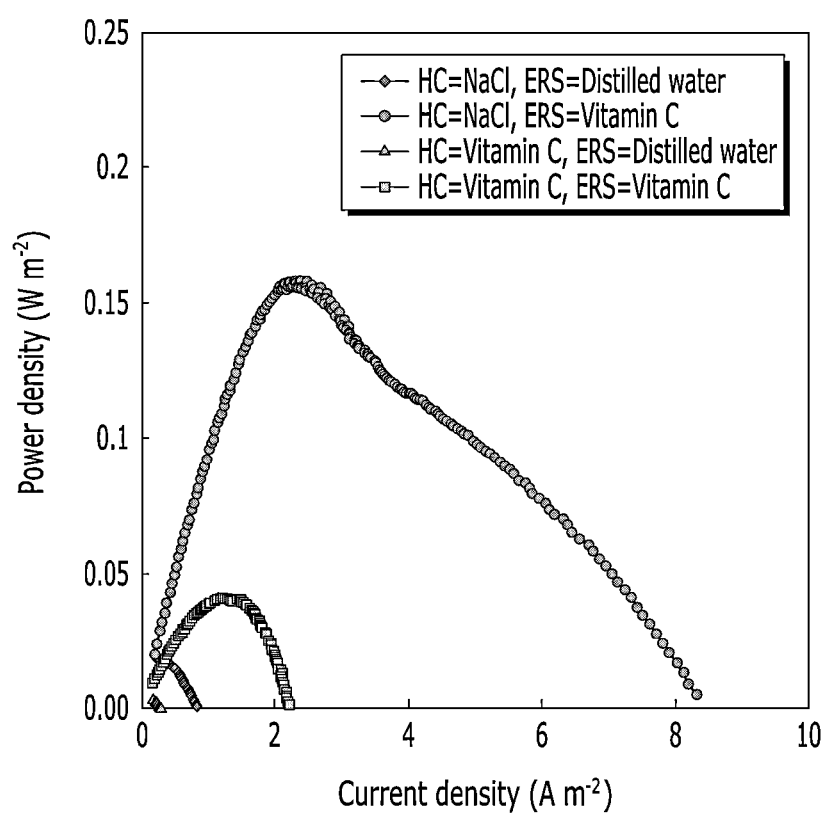
FIG. 28 is a graph illustrating a relation between a current density and a power density in the case where vitamin is applied.

For the test, a unit cell of 2×2 cm² was formed. As shown in the result, NaCl and ascorbic acid were used as a high-concentration solution, and normal fresh water and ascorbic acid were used as an electrode electrolyte solution. The result is illustrated in FIG. 28. From the result of FIG. 28, it can be seen that ascorbic acid may be used as the electrode electrolyte solution, and it can be seen that even in the case where ascorbic acid is used as the high-concentration solution, it is possible to generate power in the level of ⅓ of NaCl.

Electricity Generation Test in General Stack

Figure 29:
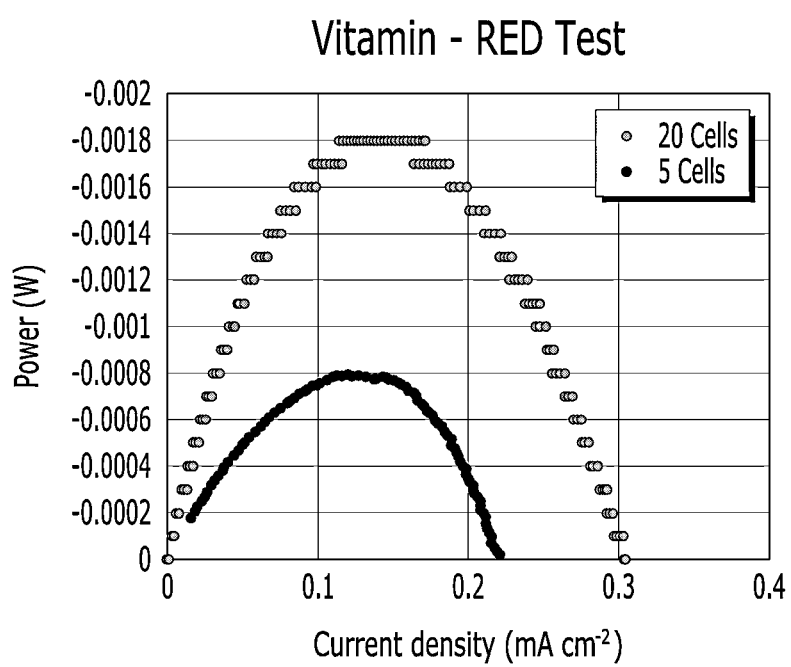
FIG. 29 is a graph illustrating a relation between a current density and power in the case where vitamin is applied.

The result is illustrated in FIG. 29. Only ascorbic acid was used as an electrode electrolyte solution and a high-concentration solution used, and water was used as a low-concentration solution. As the unit cell, five cells and 20 cells were used. From the result of FIG. 29, generated power is in the level of 0.8 to 1.8 mW.

Electricity Generation Test in General Stack

Figure 30:
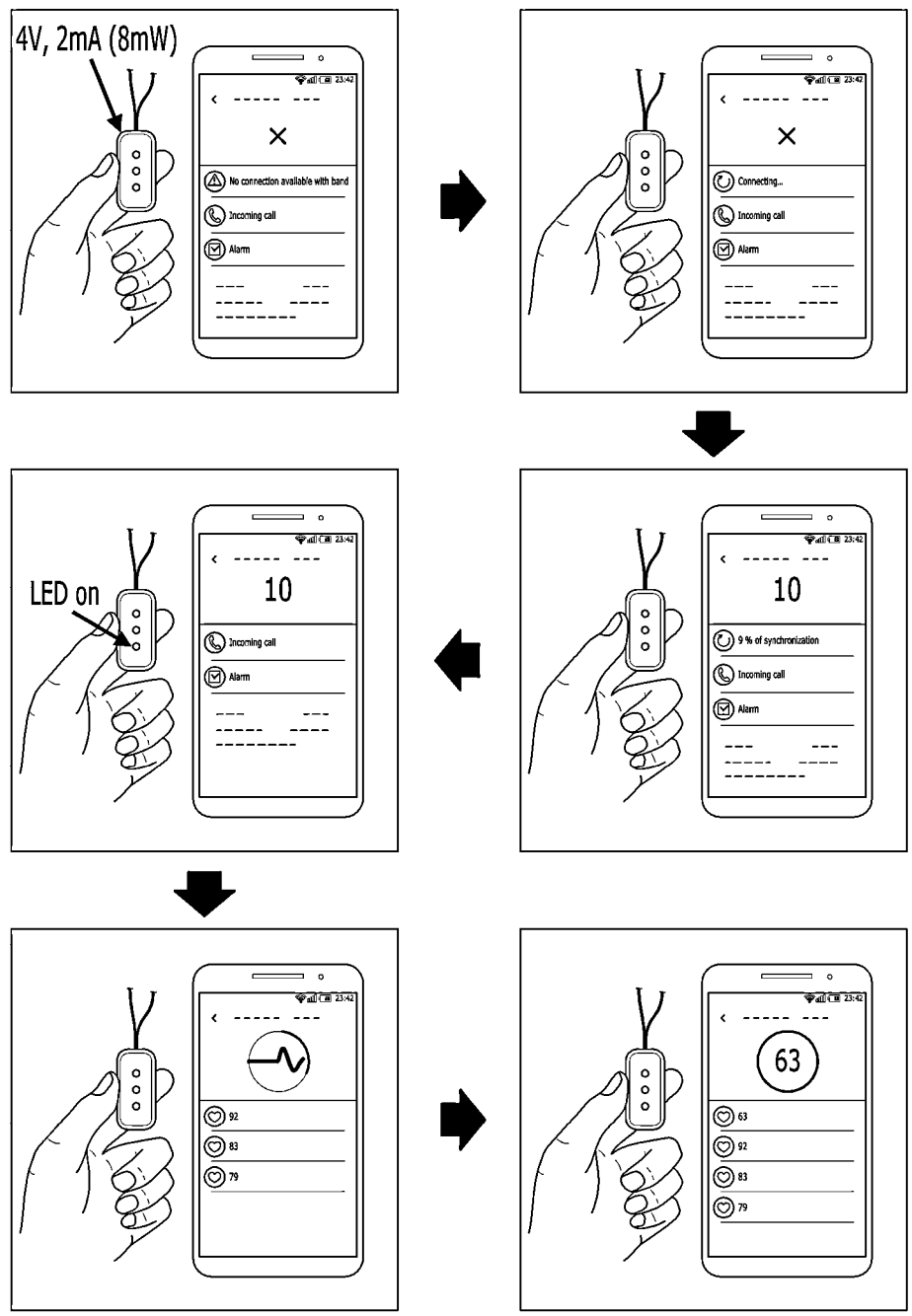
FIG. 30 is an image illustrating that it is possible to supply a power source to a sensor with a general RED stack to which vitamin is applied.

The result is illustrated in FIG. 30. A sensor, which has a voltage of 3.0 to 4 V and a maximum current value consumed for measuring pulse is 2 mA, was manufactured and used, measured pulse as a bio-signal, and used a method of transmitting a result value of the measurement to an application of a mobile phone through wireless communication (Bluetooth), and only ascorbic acid was used as an electrode electrolyte solution and high-concentration nutrients for salinity gradient power generation for supply power. From the result of FIG. 30, it can be seen that the measured pulse is 63 times, and using ascorbic acid alone, it is possible not only to measure a bio-signal (pulse) but also to generate power so that the result is directly transmitted to a mobile application through wireless communication.

Figure 31:
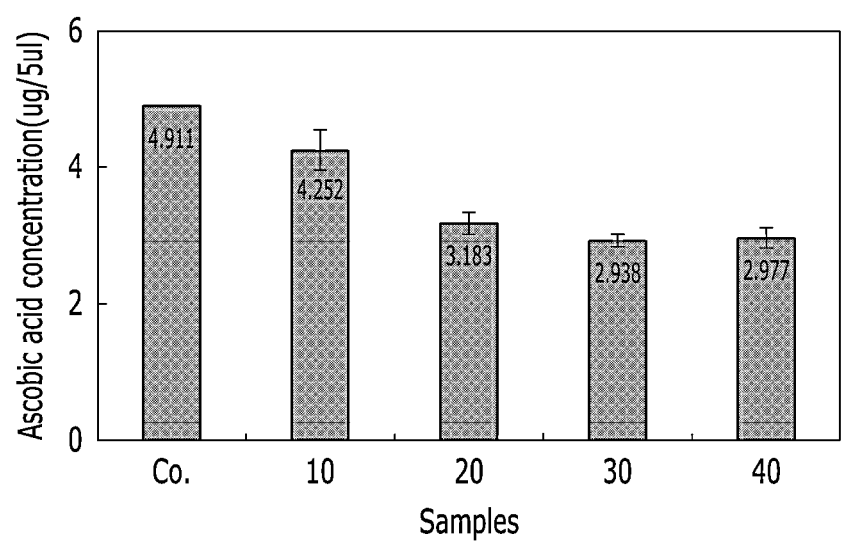
FIG. 31 is an image illustrating the degree of ascorbic acid contained in a low-concentration collected solution discharged through reverse electrodialysis salinity gradient power generation.

FIG. 31 is an image illustrating the degree of ascorbic acid contained in a low-concentration collected solution discharged through reverse electrodialysis salinity gradient power generation. For the measurement, a sample solution of 5 ul was mixed with ethanol together with DPPH. After the incubation at a room temperature for 30 minutes, absorbance at 517 nm was analyzed. For accuracy of the experiment, a standard value of an ascorbic acid solution for each concentration was calculated in advance. For the samples used for the measurement, lower-concentration supply solutions were 10, 20, 30, 40, and 50 ml/min, and a high-concentration solution (ascorbic acid) was 50 ml/min. As the result of the measurement, there is a slight difference according to the flow rate of the low-concentration solution, but it can be seen that ascorbic acid is obviously presented in the low-concentration solution. This means that electricity may be generated through the reverse electrodialysis salinity gradient power generation and the used ascorbic acid was transferred to the low-concentration solution through the ion-exchange membrane without deterioration and change.

In the foregoing, the exemplary embodiments of the present invention has been described, and particularly, the case where the electricity generation and nutrient and/or drug delivery module is formed of two reverse electrodialysis devices has been described as the example, but the electricity generation and nutrient and/or drug delivery module may be formed of one reverse electrodialysis device as a matter of course. Further, the present invention is not limited by the exemplary embodiment of the present invention and may be modified and carried out in various forms within the range of the claims, the detailed description of the invention, and the accompanying drawings, and the modifications also belong to the scope of the present invention as a matter of course.

INDUSTRIAL APPLICABILITY

The present invention is applicable to the fields of medical, healthcare, beauty, and the like.

The invention claimed is:

1. An energy self-sufficient system based on salinity gradient power generation, comprising:
a first Reverse Electro Dialysis (RED) pad and a second RED pad each configured to generate electricity by using a nutrient and/or drug solution;
a water supply unit configured to supply water to the first RED pad and the second RED pad,
the first RED pad comprising:
a first pad supporting body formed with a first electrode pattern,
a second pad supporting body formed with a second electrode pattern disposed below the first pad supporting body,
a first skin contact delivery unit disposed below the second pad supporting body,
a plurality of RED unit cells arranged between the first pad supporting body and the second pad supporting body, and electrically connected to the first electrode pattern and the second electrode pattern, and
a first terminal disposed on the second pad supporting body and configured to apply a first polarity to the first skin contact delivery unit by being electrically connected to one of the plurality of RED unit cells,
the second RED pad comprising:

a third pad supporting body formed with a third electrode pattern, a fourth pad supporting body formed with a fourth electrode pattern disposed below the third pad supporting body, a second skin contact delivery unit disposed below the fourth pad supporting body, a plurality of RED unit cells arranged between the third pad supporting body and the fourth pad supporting body, and electrically connected to the third electrode pattern and the fourth electrode pattern, and a second terminal disposed on the fourth pad supporting body and configured to apply a second polarity to the second skin contact delivery unit by being electrically connected to one of the plurality of RED unit cells of the second RED pad, wherein, the water supply unit is disposed on the first pad supporting body of the first RED pad, and the third pad supporting body of the second RED pad, and supplies water to the plurality of RED unit cells of the first RED pad and the plurality of RED unit cells of the second RED pad.

2. The energy self-sufficient system based on salinity gradient power generation of claim 1, further comprising a first external input terminal having an opposite polarity to the first terminal and electrically connected the first RED pad;

a second external input terminal having an opposite polarity to the second terminal and electrically connected the second RED pad; and a bio-signal measuring unit connected to the first and second external input terminals and configured to measure a bio-signal by receiving electricity from the first RED pad, and the second RED pad.

3. The energy self-sufficient system based on salinity gradient power generation of claim 1, wherein the nutrients and/or drugs are vitamins, nutritional fluids, skin regenerating agents, heart rate regulating drugs, thermoregulation agents, anti-inflammatory agents, blood pressure regulating drugs, bone regenerative drugs, blood sugar regulating drugs, neuroregenerating agents, ionized nutrients, or complexes thereof.

4. The energy self-sufficient system based on salinity gradient power generation of claim 1, wherein the nutrients and/or drugs are embedded within a porous pattern formed on an ion exchange membrane of the plurality of RED unit cells of the first RED pad and the second RED pad.

5. The energy self-sufficient system based on salinity gradient power generation of claim 1, wherein each of the plurality of RED unit cells of the first RED pad and the second RED pad comprises a cell stack arranged between the first electrode pattern and the second electrode pattern in which cation-exchange membranes and anion-exchange membranes are alternately arranged, and a gasket disposed between the cation-exchange membranes and anion-exchange membranes, and between the membranes and the electrode to prevent water and the nutrients within each of the plurality of unit cells of the first RED pad and the plurality of RED unit cells of the second RED pad from leaking to the outside.

6. The energy self-sufficient system based on salinity gradient power generation of claim 1, wherein the first skin contact delivery unit and a second skin contact delivery unit further includes additional nutrients and/or drugs.

7. The energy self-sufficient system based on salinity gradient power generation of claim 1, wherein the first skin contact delivery unit of the first RED pad further includes additional nutrients and/or drugs that have the first polarity within a first solution; and the second skin contact delivery unit of the second RED pad further includes additional nutrients and/or drugs that have the second polarity within a second solution.

8. The energy self-sufficient system based on salinity gradient power generation of claim 1, further comprising a central control device configured to receive a signal measured from a bio-signal measuring unit, analyze a state of a body according to the received signal, control driving of the first and second RED pads, or control driving of the bio-signal measuring sensor unit.

* * * * *